(12) United States Patent
Douglas

(10) Patent No.: US 10,964,095 B1
(45) Date of Patent: Mar. 30, 2021

(54) METHOD AND APPARATUS FOR TANDEM VOLUME RENDERING

(71) Applicant: Robert Edwin Douglas, Winter Park, FL (US)

(72) Inventor: Robert Edwin Douglas, Winter Park, FL (US)

(*) Notice: Subject to any disclaimer, the term of this patent is extended or adjusted under 35 U.S.C. 154(b) by 0 days.

(21) Appl. No.: 17/033,892

(22) Filed: Sep. 27, 2020

Related U.S. Application Data

(63) Continuation-in-part of application No. 16/936,293, filed on Jul. 22, 2020, and a continuation-in-part of application No. 16/879,758, filed on May 21, 2020, now Pat. No. 10,776,989, and a continuation-in-part of application No. 16/842,631, filed on Apr. 7, 2020.

(51) Int. Cl.
| | |
|---|---|
| *G06T 15/08* | (2011.01) |
| *G06T 7/00* | (2017.01) |
| *G06T 17/10* | (2006.01) |
| *G06T 7/11* | (2017.01) |
| *G02B 27/01* | (2006.01) |

(52) U.S. Cl.
CPC .......... *G06T 15/08* (2013.01); *G02B 27/0172* (2013.01); *G06T 7/0012* (2013.01); *G06T 7/11* (2017.01); *G06T 17/10* (2013.01); *G02B 2027/014* (2013.01); *G02B 2027/0138* (2013.01)

(58) Field of Classification Search
CPC .......................... G06T 15/08; G06T 2210/41
See application file for complete search history.

(56) References Cited

U.S. PATENT DOCUMENTS

| | | | |
|---|---|---|---|
| 10,755,474 B1* | 8/2020 | Schneider | G06T 15/08 |
| 2008/0094397 A1* | 4/2008 | Li | G06T 15/08 345/427 |
| 2015/0309264 A1* | 10/2015 | Abovitz | G02B 6/32 385/33 |
| 2016/0026266 A1* | 1/2016 | Douglas | A61B 5/055 345/157 |
| 2018/0357814 A1* | 12/2018 | Bohn | G06T 15/005 |
| 2019/0228524 A1* | 7/2019 | Chen | G16H 30/20 |
| 2020/0265632 A1* | 8/2020 | Kredi | G06T 15/08 |

* cited by examiner

*Primary Examiner* — Ross Varndell

(57) ABSTRACT

This patent provides a method for performing advanced volume rendering strategies. In tandem volume rendering, the volume is divided and a first portion of the volume undergoes a first volume rendering strategy and a second portion undergoes a second volume rendering strategy. Additional volume rendering strategies disclosed herein include preemptive volume rendering.

20 Claims, 23 Drawing Sheets

DIVIDING VOLUME BY CONVERGENCE POINT

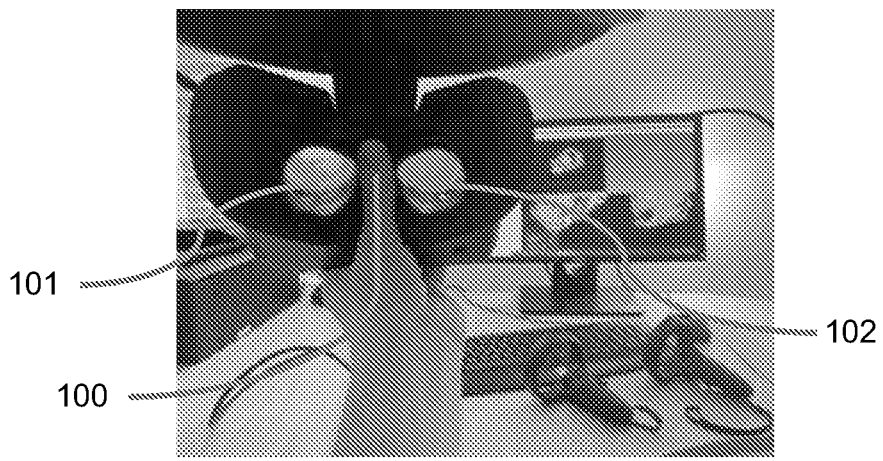
PRIOR ART   Fig. 1A
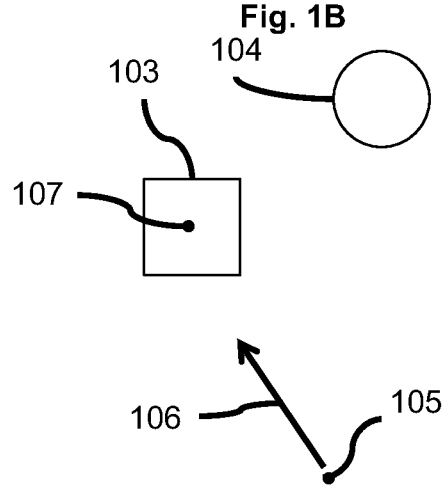
Fig. 1B
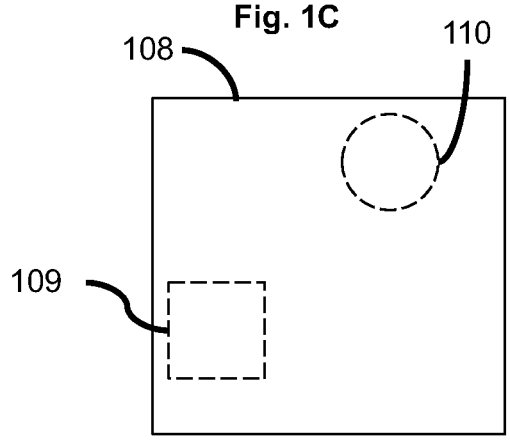
Fig. 1C
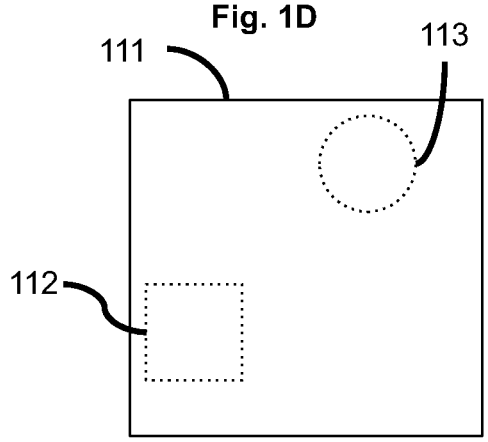
Fig. 1D
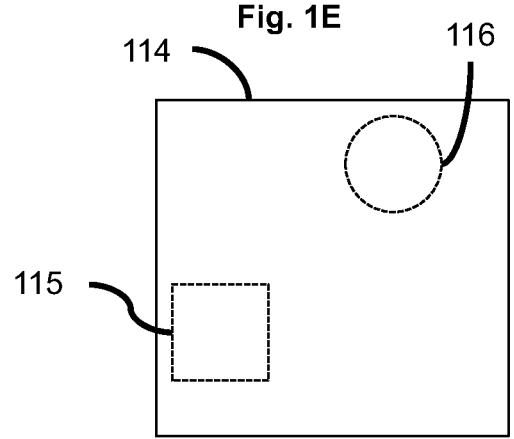
Fig. 1E

Methods of dividing the volume

- Segmentation (e.g., segment liver, segment contiguous structures)
- Checklist item (e.g., liver, spleen, etc.)
- Eye factors:
    - Eye tracking metrics (e.g., convergence point of a user. For example, identify where the user is looking in the volume (e.g., convergence point) and divide the volume in to a first portion (close to the convergence point) and a second portion (far from the convergence point)
    - Monocular or binocular viewing (e.g., is the object seen by both eyes or just by one of the two eyes. See US Patent #10,657,731)
- By location in the field of view
- Analysis methods (e.g., Artificial intelligence (AI))
- Property of a segmented object: e.g.,
    - Shape (e.g., round shaped, irregular shaped, etc.)
    - Size (e.g., smaller than 1 $cm^3$, larger than 1 $cm^3$, etc.)
    - Margins (e.g., smooth, ill-defined, spiculated, etc.)
    - Internal architecture (e.g., homogeneous, heterogeneous, etc.)
    - Prioritization (as described in US Patent 10,766,989)
- Timing (e.g., rendering type is determined by timing factors)
- Based on property of a structure:
    - Priority level (A METHOD AND APPARATUS FOR PRIORITIZED VOLUME RENDERING, US Patent 10,776,989)
- Combination of the above

Figure 3

DIVIDING VOLUME BY SEGMENTED ITEM ON CHECKLIST

DIVIDING VOLUME BY LOCATION WITHIN VOLUME

DIVIDING VOLUME BY DETERMINING WHICH OBJECT IS BEING EXAMINED

DIVIDING VOLUME BY CONVERGENCE POINT

DIVIDING VOLUME BY CONVERGENCE POINT

DIVIDING VOLUME BY ARTIFICIAL INTELLIGENCE ALGORITHM

DIVIDING VOLUME BY PRIORITIZATION
Fig. 11A CLUSTER OF MICROCALCIFICATIONS
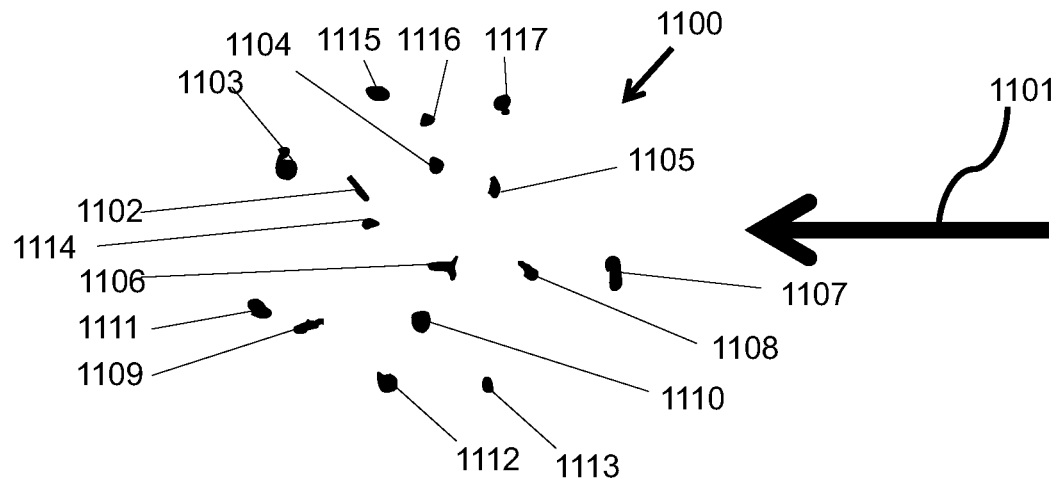
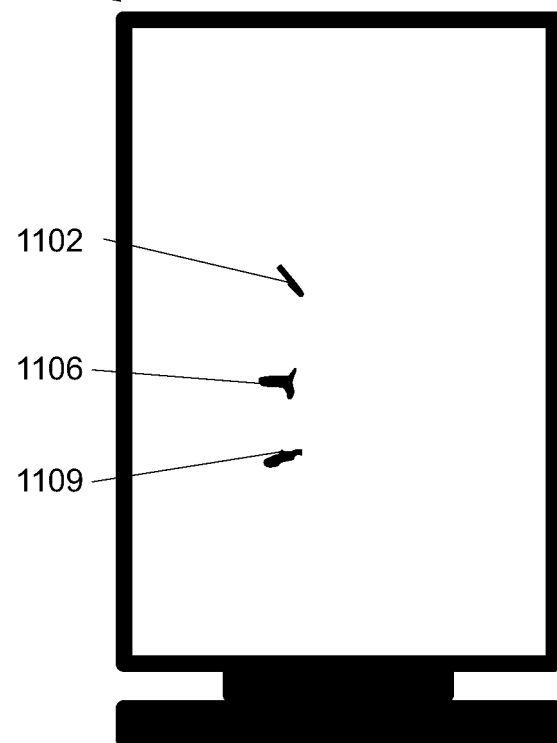
Fig. 11B FIRST PORTION OF VOLUME
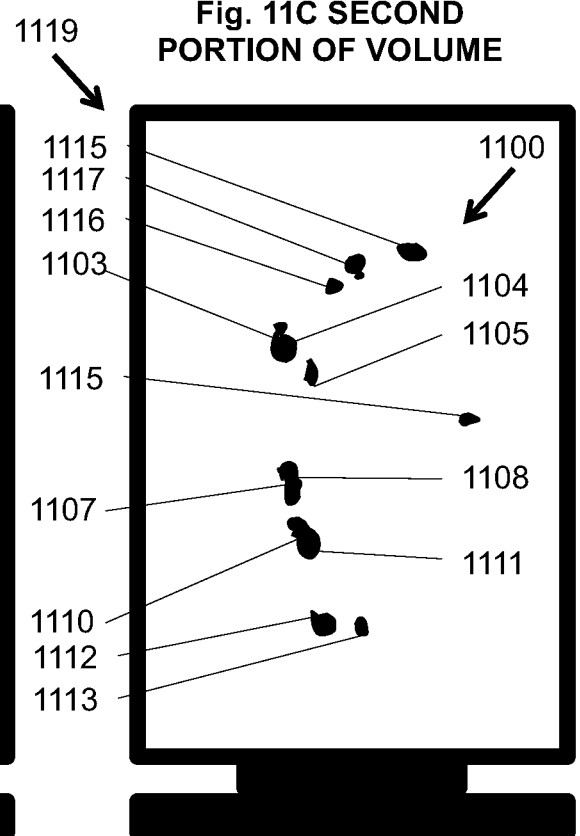
Fig. 11C SECOND PORTION OF VOLUME

DIVIDING VOLUME BY IMAGING FEATURE
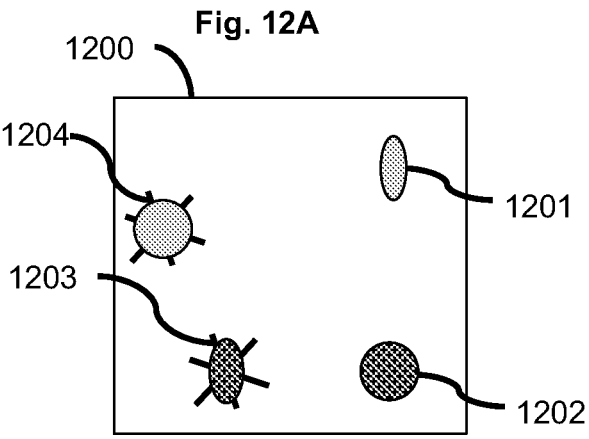
Fig. 12A
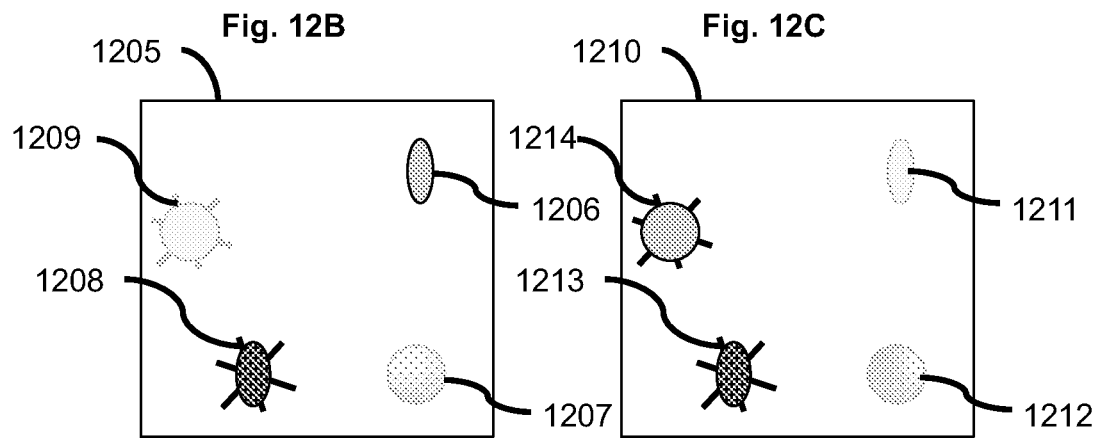
Fig. 12B
Fig. 12C
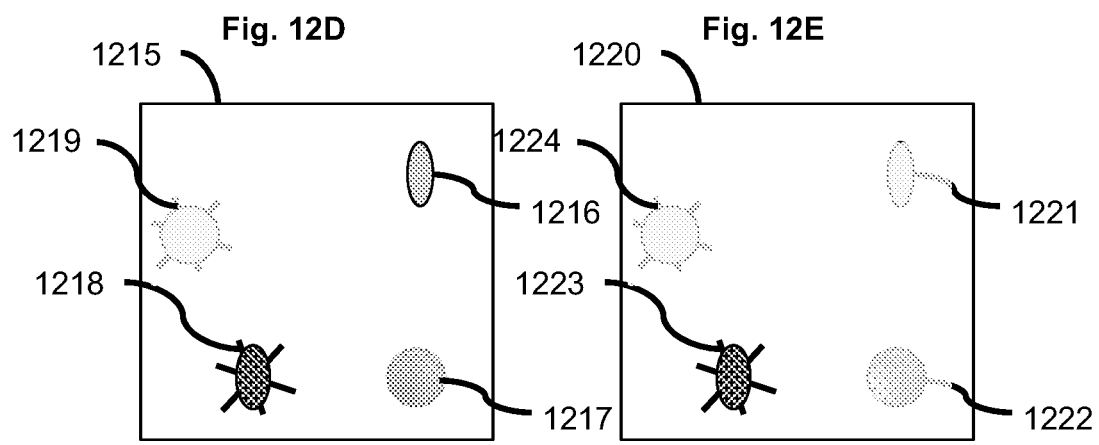
Fig. 12D
Fig. 12E

**FACTORS USED TO DETERMINE THE PREFERRED TYPE OF
RENDERING FOR A STRUCTURE WITHIN THE VOLUME**

Factors used to determine the preferred type of rendering for a structure within the volume

- Imaging features: e.g., properties of a segmented object
    - Shape (e.g., round shaped, irregular shaped, etc.)
    - Size (e.g., smaller than 1 cm$^3$, larger than 1 cm$^3$, etc.)
    - Margins (e.g., smooth, ill-defined, spiculated, etc.)
    - Internal architecture (e.g., homogeneous, heterogeneous, etc.)
    - Prioritization (as described in US Patent 10,766,989)
- Analysis methods (e.g., Artificial intelligence (AI))
- Timing (e.g., rendering type is determined by timing factors)
- Desired field of view
- Computer(s) available (e.g., first computer performs rendering of the first portion, second computer performs rendering of the second portion, etc.)

EACH STRUCTURE MAY HAVE A PREFERRED TYPE OF RENDERING

Examples of ways a segmented structure (e.g., vascular structure) can be rendered (ordered by user preference)
1 Preferred option: Model the volume as very (sub-1 mm) small voxels and perform false light to achieve shading
- Rationale #1: if user zooms in, then the voxels will not appear cube-like
- Rationale #2: False light with shading provides an improved monocular depth cue

2 Preferred option: Enlarge voxels
(e.g., 1 mm isotropic)
- Rationale: minimally degrades image quality

3 Preferred option: Model the volume as a point cloud
- Rationale #1: Very fast rendering

1400

Examples of ways a segmented structure (e.g., terrain) can be rendered (ordered by user preference)
1 Preferred option: Model the volume as very small voxels
2 Preferred option: Model the volume as polygon mesh
3 Preferred option: Model the volume as a point cloud

CONVENTIONAL AND ADVANCED RENDERING

Conventional and advanced rendering

- Conventional rendering methods (voxel rendering, point cloud rendering, polygon mesh rendering)
- Advanced rendering methods:
  - Tandem dynamic rendering
  - Transparent rendering
  - Partial image rendering
  - Pre-emptive volume rendering
    - Predictive-type preemptive volume rendering
    - Nonpredictive-type preemptive volume rendering
  - Recalled volume rendering

DYNAMIC TANDEM RENDERING

Fig. 17A

| Segmented structure | Property #1 (e.g., size) | Property #2 (e.g., shape) | #1 Preferred rendering | #2 Preferred rendering | #3 Preferred rendering |
|---|---|---|---|---|---|
| Object #1 (e.g., stone in bladder) | 1.05 cm$^3$ | round | Voxel rendering | Polygon mesh | Point cloud |
| Object #2 (e.g., tumor in bladder) | 2.01 cm$^3$ | irregular, spiculated | Voxel rendering | Polygon mesh | Point cloud |
| Object #3 (e.g., foley balloon in bladder) | 3.96 cm$^3$ | oval | Voxel rendering | Polygon mesh | Point cloud |

Fig. 17B

| Segmented structure | Property #1 (e.g., size) | Property #2 (e.g., shape) | #1 Preferred rendering | #2 Preferred rendering | #3 Preferred rendering |
|---|---|---|---|---|---|
| Object #1 (e.g., stone in bladder) | 1.05 cm$^3$ | round | Voxel rendering | Polygon mesh | Point cloud |
| Object #2 (e.g., tumor in bladder) | 2.01 cm$^3$ | irregular, spiculated | Voxel rendering | Polygon mesh | Point cloud |
| Object #3 (e.g., foley balloon in bladder) | 3.96 cm$^3$ | oval | Voxel rendering | Polygon mesh | Point cloud |

PARTIAL IMAGE RENDERING

PREEMPTIVE VOLUME RENDERING

| Image | Viewpoint | Viewing angle | Volume |
|---|---|---|---|
| 1 | (x=100, y,=100, z=100) | (α=90°, Θ=0°) | Vasculature of brain only |
| 2 | (x=101, y,=100, z=100) | (α=90°, Θ=0°) | Vasculature of brain only |
| 3 | (x=102, y,=100, z=100) | (α=90°, Θ=0°) | Vasculature of brain only |
| 4 | (x=103, y,=100, z=100) | (α=90°, Θ=0°) | Vasculature of brain only |
| 5 | (x=104, y,=100, z=100) | (α=90°, Θ=0°) | Vasculature of brain only |

METHOD AND APPARATUS FOR TANDEM VOLUME RENDERING

TECHNICAL FIELD

Aspects of this disclosure are generally related to 3D imaging, and more specifically the image processing thereof.

BACKGROUND

Medical imaging datasets are large. Optimized viewing of the data can result in improved diagnostic accuracy and improved surgical planning. Recently, in effort to overcome the challenge of rendering large datasets, U.S. patent application Ser. No. 16/927,886, A METHOD AND APPARATUS FOR GENERATING A PRECISION SUB-VOLUME WITHIN THREE-DIMENSIONAL IMAGE DATASETS, was filed on Jul. 13, 2020. Overall, this helps image analysis by generating a precise sub-volume within a large dataset from which rendering can be performed.

SUMMARY

All examples, aspects and features mentioned in this document can be combined in any technically possible way.

The purpose of this invention is to improve rendering of volumes. This invention discloses a method comprising: diving a volumetric dataset into a first portion and at least one additional portion; performing a first type of rendering for the first portion; and performing a second type of rendering for the second portion wherein the first type of rendering is different from the second type of rendering.

Some embodiments comprise wherein the first type of rendering has a first processing speed and the second type of rendering has a second processing speed.

Some embodiments comprise wherein the first portion is determined by a radius around a user's convergence point.

Some embodiments comprise wherein the first portion is determined by a segmented object located at user's convergence point.

Some embodiments comprise wherein the portions is determined a binocular field of view and wherein the second portion is determined by a monocular field of view.

Some embodiments comprise wherein the first portion is determined a segmented item on a checklist.

Some embodiments comprise wherein the first portion is determined a location within the volume.

Some embodiments comprise wherein the first portion is determined by an artificial intelligence algorithm.

Some embodiments comprise wherein the first portion is determined by a prioritization level of an object.

Some embodiments comprise wherein the first portion is determined by at least one of the group consisting of: an imaging features of a segmented object; and, a combination of imaging features of a segmented object.

Some embodiments comprise wherein the first type of rendering is optimized for the first portion and the second type of rendering is optimized for the second portion.

Some embodiments comprise wherein the first portion is determined in a dynamic fashion.

Some embodiments comprise wherein the first portion is determined by an artificial intelligence algorithm.

Some embodiments comprise wherein the first portion is rendered in at least one of the group consisting of: partial transparent rendering; and, fully transparent rendering.

Some embodiments comprise performing predictive type preemptive volume rendering comprising the steps of: generating a predicted set of viewing parameters; rendering the volumetric dataset using the predicted set of viewing parameters to create an image; and displaying the image when the user's viewing parameters match the predicted set of viewing parameters.

Some embodiments comprise performing recall type volume rendering comprising the steps of: storing a rendered image and a set of viewing parameters associated with the rendered image; monitoring a user's viewing parameters; and displaying the rendered image when the user's viewing parameters match the set of viewing parameters associated with the rendered image.

Some embodiments comprise displaying an image generated based on performing the first type of rendering for the first portion and performing a second type of rendering for the second portion wherein the first type of rendering is different from the second type of rendering on a display. Some embodiments comprise wherein the display is a head display unit, such as a virtual reality display.

Some embodiments comprise a non-transitory computer readable medium having computer readable code thereon for image processing, the medium comprising: instructions for diving up a volumetric dataset into a first portion and at least one additional portion; instructions for performing a first type of rendering for the first portion; and instructions for performing a second type of rendering for the second portion wherein the first type of rendering is different from the second type of rendering.

Some embodiments comprise an apparatus comprising: a processor; a non-transitory memory having computer-executable instructions stored thereupon which, when executed by the processor, cause the processor to perform: diving a volumetric dataset into a first portion and at least one additional portion; performing a first type of rendering for the first portion; and performing a second type of rendering for the second portion wherein the first type of rendering is different from the second type of rendering.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides steps explained herein that when performed (e.g. when executing) on the processor, operates as explained herein within the computerized device to perform all of the method embodiments and operations explained herein as embodiments of the invention. Thus any computerized device that performs or is programmed to perform processing explained herein is an embodiment of the invention.

Other arrangements of embodiments of the invention that are disclosed herein include Software programs to perform the method embodiment steps and operations Summarized above and disclosed in detail below. More particularly, a computer program product is one embodiment that has a computer-readable medium including computer program logic encoded thereon that when performed in a computerized device provides associated operations providing steps as explained herein.

The computer program logic, when executed on at least one processor with a computing system, causes the processor to perform the operations (e.g., the methods) indicated herein as embodiments of the invention. Such arrangements of the invention are typically provided as Software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other Such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as Software and hardware, or as hardware and/or circuitry alone. Such as within a data communications device. The features of the invention, as explained herein, may be employed in data processing devices and/or Software systems for Such devices. Note that each of the different features, techniques, configurations, etc. discussed in this disclosure can be executed independently or in combination. Accordingly, the present invention can be embodied and viewed in many different ways. Also, note that this Summary section herein does not specify every embodiment and/or incrementally novel aspect of the present disclosure or claimed invention. Instead, this Summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE FIGURES

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1A illustrates showing the D3D imaging system.

FIG. 1B illustrates a viewpoint, a first viewing angle and two objects to be rendered.

FIG. 1C illustrates a first 2D image generated based on the viewpoint, the viewing angle, the convergence point, and the volume of interest, which includes the first object and the second object.

FIG. 1D illustrates a second 2D image generated based on the viewpoint, the viewing angle, the convergence point, and the volume of interest, which includes the first object and the second object.

FIG. 1E illustrates a third 2D image generated based on the viewpoint, the viewing angle, the convergence point, and the volume of interest, which includes the first object and the second object.

FIG. 3 illustrates method of dividing the volume into a first portion and at least one additional portion.

FIG. 11A illustrates a first viewing perspective looking at a cluster of microcalcifications wherein some of the microcalcifications are determined to be benign and some of the microcalcifications are determined to be suspicious.

FIG. 11B illustrates dividing the volume of microcalcifications into a first portion.

FIG. 11C illustrates dividing the volume of microcalcifications into a second portion.

FIG. 12A illustrates a volume containing four objects with each object having a unique set of imaging features.

FIG. 12B illustrates a volume containing four objects with each object having a unique set of imaging features wherein the volume is divided into a first portion based on the imaging feature of round shape and a second portion based on oval shape.

FIG. 12C illustrates a volume containing four objects with each object having a unique set of imaging features wherein the volume is divided into a first portion based on the imaging feature of smooth margins and a second portion based on spiculated margins.

FIG. 12D illustrates a volume containing four objects with each object having a unique set of imaging features wherein the volume is divided into a first portion based on the imaging feature of heterogeneous internal architecture and a second portion based on homogeneous internal architecture.

FIG. 12E illustrates a volume containing four objects with each object having a unique set of imaging features wherein the volume is divided into a first portion based on having the imaging feature of both spiculated margins and heterogeneous internal architecture and a second portion will include all segmented structures not meeting criteria for the first portion.

FIG. 13 illustrates a text box describing factors used to determine the preferred type of rendering.

FIG. 14 illustrates preferred rendering schemes for different segmented structures.

FIG. 16 illustrates a text box conventional and advanced types of rendering.

FIG. 17A illustrates tandem rendering of three objects at a first time point.

FIG. 17B illustrates tandem rendering of three objects at a second time point, which is called tandem dynamic rendering.

DETAILED DESCRIPTION

Figure 2:
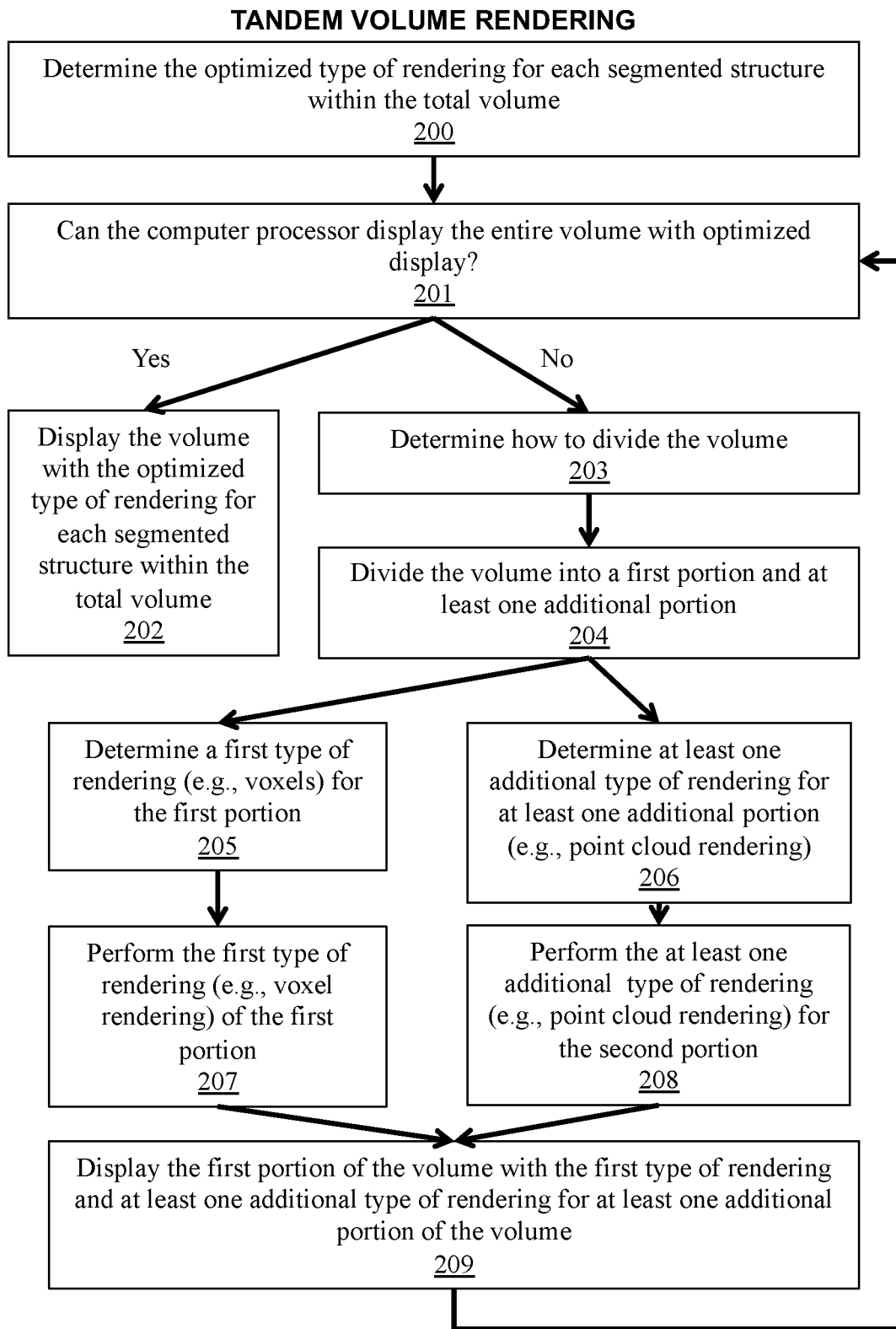
FIG. 2 illustrates a processing block for tandem volume rendering of large complex datasets.

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

FIG. 1A illustrates showing the D3D imaging system. 100 illustrates the midpoint between the eyes on a head display unit (HDU). 101 illustrates the left eye image, which is generated based on the left eye viewpoint, the viewing angle and the convergence point. This is described in U.S. Pat. Nos. 8,384,771 and 9,349,183, which are incorporated by reference. 102 illustrates the right eye viewpoint. The orientation (roll, pitch and yaw) of the HDU determines the viewing angle. The position of the HDU determines the left eye viewpoint and right eye viewpoint. The imaged displayed on the D3D viewing system performs one type of rendering for the whole scene. Even when the scene is complex, the D3D rendering engine performed only a single type of rendering. The D3D system has only ever performed voxel rendering of the entire volume.

FIG. 1B illustrates a viewpoint, a first viewing angle and two objects to be rendered. 103 illustrates a first object. 104 illustrates a second object. 105 illustrates a viewpoint. 106 illustrates a viewing angle. 107 illustrates a convergence point.

FIG. 1C illustrates a first 2D image generated based on the viewpoint, the viewing angle, the convergence point, and the volume of interest, which includes the first object and the second object. 108 illustrates the 2D image generated based on the viewpoint, the viewing angle, the convergence point, and the volume of interest in FIG. 1B, which includes the first object and the second object. This prior art process performs the same type of rendering of all portions of the volume, which in this case includes the first object and the second object. So, in this prior art example, both the first object and the second object are rendered the same way (e.g., rendering the volume as objects made of polygon mesh). 109 illustrates a portion of the image that corresponds to the first object. 110 illustrates a portion of the image that corresponds to the second object.

FIG. 1D illustrates a second 2D image generated based on the viewpoint, the viewing angle, the convergence point, and the volume of interest, which includes the first object and the second object. 108 illustrates the 2D image generated based on the viewpoint, the viewing angle, the convergence point, and the volume of interest in FIG. 1B, which includes the first object and the second object.

This prior art process performs the same type of rendering of all portions of the volume, which in this case includes the first object and the second object. So, in this prior art example, both the first object and the second object are rendered the same way (e.g., rendering the volume as points as in a point cloud). 109 illustrates a portion of the image that corresponds to the first object. 110 illustrates a portion of the image that corresponds to the second object.

FIG. 1E illustrates a third 2D image generated based on the viewpoint, the viewing angle, the convergence point, and the volume of interest, which includes the first object and the second object. 108 illustrates the 2D image generated based on the viewpoint, the viewing angle, the convergence point, and the volume of interest in FIG. 1B, which includes the first object and the second object. This prior art process performs the same type of rendering of all portions of the volume, which in this case includes the first object and the second object. So, in this prior art example, both the first object and the second object are rendered the same way (e.g., rendering the volume as voxels). 109 illustrates a portion of the image that corresponds to the first object. 110 illustrates a portion of the image that corresponds to the second object.

FIG. 2 illustrates a processing block for tandem volume rendering of large complex datasets. 200 illustrates a processing block of determining the optimized type of rendering for each segmented structure within the total volume. 201 illustrates a processing block of determining if the computer processor can display the entire volume with optimized display. 202 illustrates a processing block of displaying the volume with the optimized type of rendering for each segmented structure within the total volume which is performed if the computer can process the entire volume with the optimized display. 203 illustrates a processing block of determining how to divide the volume. 204 illustrates a processing block of dividing the volume into a first portion and at least one additional portion which is performed if the computer can process the entire volume with the optimized display. 205 illustrates a processing block of determining a first type of rendering (e.g., voxels) for the first portion. 206 illustrates a processing block of determining at least one additional type of rendering (e.g., point cloud rendering) for at least one additional portion. 207 illustrates a processing block of performing the first type of rendering (e.g., voxel rendering) of the first portion. 208 illustrates a processing block of performing the at least one additional type of rendering (e.g., point cloud rendering) for the at least one additional portion. 209 illustrates displaying the first portion of the volume with the first type of rendering and at least one additional type of rendering for at least one additional portion of the volume. This process is referred to as tandem volume rendering.

FIG. 3 illustrates method of dividing the volume into a first portion and at least one additional portion. A variety of analysis methods can be utilized to divide the volume as described herein.

A radiologist commonly works through a CT or MM scan by using a checklist on an adjacent computer monitor. The volume could be divided by checklist item. For example, assume the radiologist has currently selected the liver as the active item on the checklist. The volume could be divided into a first portion (e.g., liver) and at least one additional portion (e.g., all other non-liver structures within the volume). Note that segmentation is an important element for this strategy and can be performed by techniques described in U.S. Pat. No. 8,384,8771, METHOD AND APPARATUS FOR THREE DIMENSIONAL VIEWING OF IMAGES and U.S. patent application Ser. No. 16/842,631, A SMART SCROLLING SYSTEM. It should be noted that segmentation can be used along or in conjunction with the checklist item.

Additionally, the results of the segmentation can not only help in the dividing of the volume, but also help form the basis of the preferred rendering strategy (e.g., a structure with a flat surface can be rendered as a polygon).

Analysis of eye tracking metrics derived from an eye tracking system used in conjunction with image analysis can also be used to divide the volume. For additional details on eye tracking, please see U.S. patent application Ser. No. 16/936,293, IMPROVING VISUALIZATION OF IMAGES VIA AN ENHANCED EYE TRACKING SYSTEM. For example, eye tracking metrics (e.g., convergence point of a user) can indicate where the user is looking in the volume. The volume can be divided accordingly in to a first portion (close to the convergence point) and a second portion (far from the convergence point). Furthermore, the volume can be divided based on whether viewing is monocular or binocular (e.g., answering the question "is the object seen by both eyes or just by one of the two eyes?"). See U.S. Pat. No. 10,657,731, PROCESSING 3D MEDICAL IMAGES TO ENHANCE VISUALIZATION.

Additionally, the volume may be divided by location in the field of view. For example, portions in the center of the volume could be divided into a first portion and portions in the periphery could be divided into at least one additional portion.

Additionally, Artificial intelligence (AI) algorithms can be utilized to divide the volume into a first portion and a second portion. This can be performed by using techniques described in PCT/US2019/023968, Radiologist Assisted Machine Learning. For example, the property of a segmented object can be used. For example, the following imaging features can be assigned to categorical variables and then based on an analysis, the type of rendering can be performed. For example, the shape (e.g., round shaped, irregular shaped, etc.) of a lesion can be utilized to generate rules. For example, a spiculated lesion could always be rendered with voxel rendering. A small lesion (e.g., smaller than 1 $cm^3$ could always be rendered with a voxel rendering strategy. Features of margins (e.g., smooth, ill-defined, spiculated, etc.) can be utilized to determine the type of rendering. Radiomics analysis of the internal architecture (e.g., homogeneous, heterogeneous, etc.) can be utilized to determine the type of rendering. Prioritization (as described in U.S. Pat. No. 10,766,989, A METHOD AND APPARATUS FOR PRIORITIZED VOLUME RENDERING) can be utilized to determine the type of rendering.

Additionally, the timing (e.g., rendering type is determined by timing factors). For example, the first portion could be rendered with point cloud rendering during a first time interval and with voxel rendering during a second time interval.

Various combinations of the above can be used to divide the volume into a first portion and at least one additional portion.

Figure 4A:
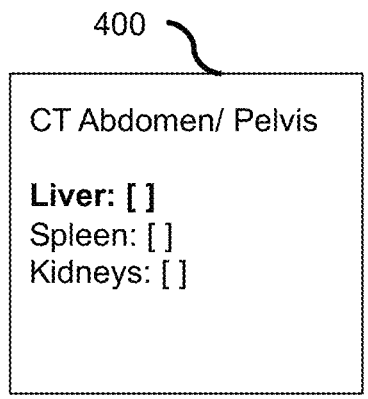
FIG. 4A illustrates a checklist, which is used in conjunction to divide the volume.

FIG. 4A illustrates a checklist, which is used in conjunction to divide the volume. 400 illustrates a sample radiology report. Note that "Liver: [ ]" is bold, which illustrates that a radiologist is actively working on the liver portion of the checklist. In this example, the total imaging volume of the CT scan of the abdomen and pelvis is divided into a first portion of the liver and a second portion of all remaining structures (other than the liver) in the volume.

Figure 4B:
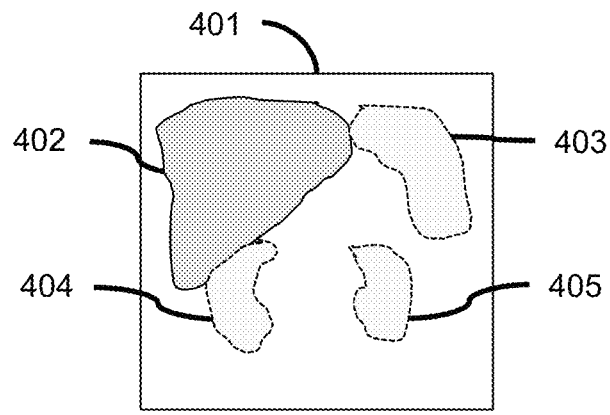
FIG. 4B illustrates dividing the volume by a first checklist item. In this method, the volume is segmented.

FIG. 4B illustrates dividing the volume by a first checklist item. In this method, the volume is segmented. The item of the checklist is used to determine the portion of the volume that receives the optimized volume rendering. The remaining portions of the volume (e.g., areas other than items on the checklist) can be rendered with non-optimized types of rendering. 401 illustrates the image. 402 illustrates the liver, which is shown in the greatest possible detail (e.g., voxel rendering at 60 Hz) due to the fact that the liver is the first portion of the volume, which is optimized. 403 illustrates the spleen, which is shown in lower detail (e.g., point cloud rendering at 30 Hz) due to the fact that the spleen is included in the second portion of the volume, which is not optimized. 404 illustrates the right kidney, which is shown in lower detail (e.g., point cloud rendering at 30 Hz) due to the fact that the right kidney is included in the second portion of the volume, which is not optimized. 405 illustrates the left kidney, which is shown in lower detail (e.g., point cloud rendering at 30 Hz) due to the fact that the left kidney is included in the second portion of the volume, which is not optimized. In this example, the rendering that was performed for the first portion and the second portion of the volume differed by the both the type of rendering and the rate of rendering.

Figure 4C:
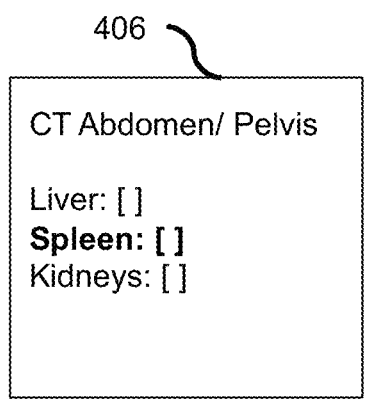
FIG. 4C illustrates a checklist, which is used in conjunction to divide the volume.

FIG. 4C illustrates a checklist, which is used in conjunction to divide the volume. 406 illustrates a sample radiology report. Note that "Spleen: [ ]" is bold, which illustrates that a radiologist is actively working on the spleen portion of the checklist. In this example, the total imaging volume of the CT scan of the abdomen and pelvis is divided into a first portion of the spleen and a second portion of all remaining structures (other than the liver) in the volume. FIG. 4C could be a subsequent time point as compared to FIG. 4A.

Figure 4D:
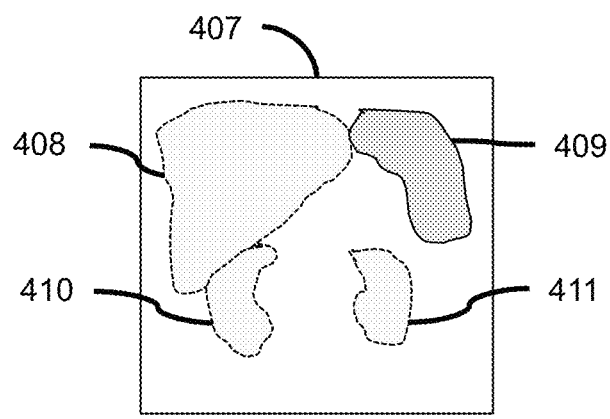
FIG. 4D illustrates dividing the volume by a second checklist item. In this method, the volume is segmented.

FIG. 4D illustrates dividing the volume by a second checklist item. In this method, the volume is segmented. The item of the checklist is used to determine the portion of the volume that receives the optimized volume rendering. The remaining portions of the volume (e.g., areas other than items on the checklist) can be rendered with non-optimized types of rendering. 407 illustrates the image. 408 illustrates the liver, which is shown in lower detail (e.g., point cloud rendering at 30 Hz) due to the fact that the liver is, in this time point, the second portion of the volume, which is not optimized. 409 illustrates the spleen, which is shown in the greatest possible detail (e.g., voxel rendering at 60 Hz) due to the fact that the spleen is in this time point, the first portion portion of the volume, which is optimized. 410 illustrates the right kidney, which is shown in lower detail (e.g., point cloud rendering at 30 Hz) due to the fact that the right kidney is included in the second portion of the volume, which is not optimized. 411 illustrates the left kidney, which is shown in lower detail (e.g., point cloud rendering at 30 Hz) due to the fact that the left kidney is included in the second portion of the volume, which is not optimized.

In this example, the rendering that was performed for the first portion and the second portion of the volume differed by the both the type of rendering and the rate of rendering.

Figure 4E:
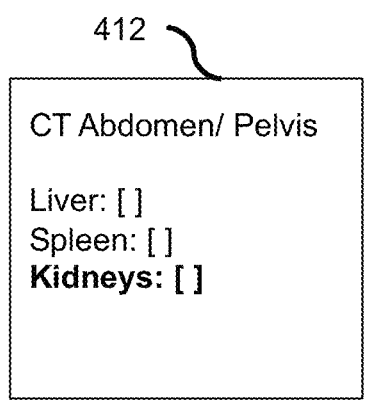
FIG. 4E illustrates a checklist, which is used in conjunction to divide the volume.

FIG. 4E illustrates a checklist, which is used in conjunction to divide the volume. 412 illustrates a sample radiology report. Note that "Kidneys: [ ]" is bold, which illustrates that a radiologist is actively working on the spleen portion of the checklist. In this example, the total imaging volume of the CT scan of the abdomen and pelvis is divided into a first portion of the kidneys and a second portion of all remaining structures (other than the liver) in the volume. FIG. 4E could be a subsequent time point as compared to FIG. 4C and FIG. 4A.

Figure 4F:
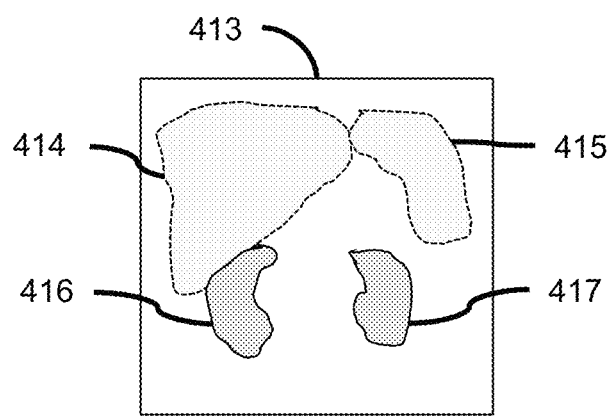
FIG. 4F illustrates dividing the volume by a second checklist item. In this method, the volume is segmented.

FIG. 4F illustrates dividing the volume by a second checklist item. In this method, the volume is segmented. The item of the checklist is used to determine the portion of the volume that receives the optimized volume rendering. The remaining portions of the volume (e.g., areas other than items on the checklist) can be rendered with non-optimized types of rendering. 413 illustrates the image. 414 illustrates the liver, which is shown in lower detail (e.g., point cloud rendering at 30 Hz) due to the fact that the liver is, in this time point, the second portion of the volume, which is not optimized. 415 illustrates the spleen, which is shown in lower detail (e.g., point cloud rendering at 30 Hz) due to the fact that the spleen is included in the second portion of the volume, which is not optimized. 416 illustrates the right kidney, which is shown in the greatest possible detail (e.g., voxel rendering at 60 Hz) due to the fact that the right kidney is included in this time point in the first portion of the volume, which is optimized. 417 illustrates the left kidney, which is shown in the greatest possible detail (e.g., voxel rendering at 70 Hz) due to the fact that the left kidney is included in this time point in the first portion of the volume, which is optimized. In this example, the rendering that was performed for the first portion and the second portion of the volume differed by the both the type of rendering and the rate of rendering.

Figure 5A:
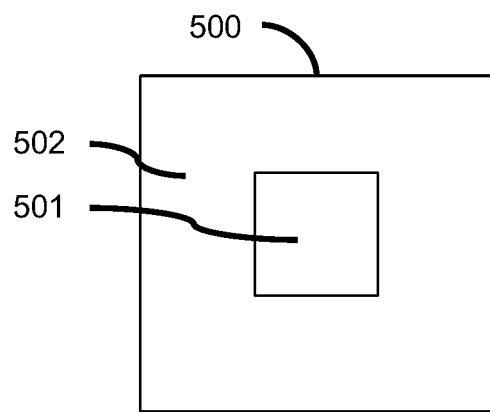
FIG. 5A illustrates a first example of dividing the field of view into a first portion and at least one additional portion by location within the field of view.

FIG. 5A illustrates a first example of dividing the field of view into a first portion and at least one additional portion by location within the field of view. 500 illustrates an image, which is divided into a first portion 501 and a second portion 502 based on location. In this example, the first portion 501 is square shaped and located in the center portion of the image 500. The second portion 502 is located in outer portions of the image 500.

Figure 5B:
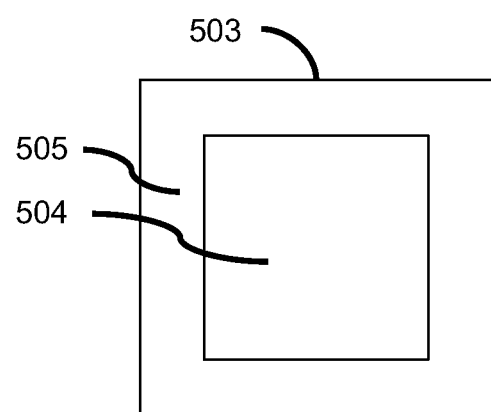
FIG. 5B illustrates a second example of dividing the field of view into a first portion and at least one additional portion by location within the field of view.

FIG. 5B illustrates a second example of dividing the field of view into a first portion and at least one additional portion by location within the field of view. 503 illustrates an image, which is divided into a first portion 504 and a second portion 505 based on location. In this example, the first portion 504 is square shaped and located in the center portion of the image 503. Note that the size of the first portion 504 is larger in FIG. 5B as compared to the first portion 501 in FIG. 5A. This could be performed at a second time interval. For example, assuming that the user has not moved their head or changed their gaze. The optimum volume rendering strategy could be worked from the inside (e.g., small square first) to the outside (e.g., large square second). The second portion 505 is located in outer portions of the image 503. Therefore, timing can be coupled with location to determine optimized volume rendering strategies.

Figure 5C:
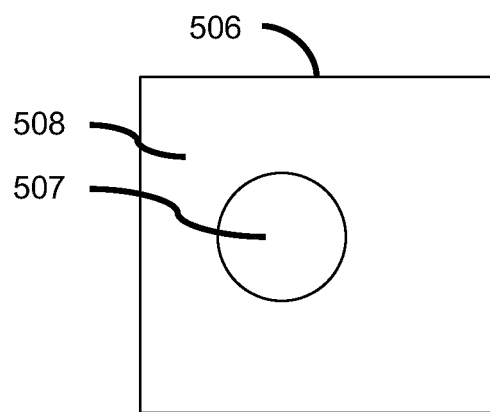
FIG. 5C illustrates a third example of dividing the field of view into a first portion and at least one additional portion by location within the field of view.

FIG. 5C illustrates a third example of dividing the field of view into a first portion and at least one additional portion by location within the field of view. 506 illustrates an image, which is divided into a first portion 507 and a second portion 508 based on location. In this example, the first portion 504 is circular shaped and located in the center portion of the image 506. The second portion 508 is located in outer portions of the image 506.

Figure 5D:
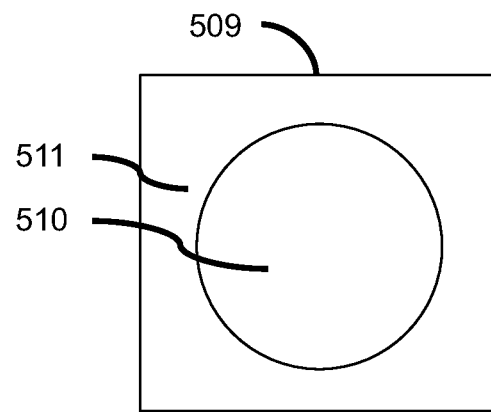
FIG. 5D illustrates a fourth example of dividing the field of view into a first portion and at least one additional portion by location within the field of view.

FIG. 5D illustrates a fourth example of dividing the field of view into a first portion and at least one additional portion by location within the field of view. 509 illustrates an image, which is divided into a first portion 510 and a second portion 511 based on location. In this example, the first portion 510 is circular shaped and located in the center portion of the image 509. Note that the size of the first portion 510 is larger in FIG. 5D as compared to the first portion 507 in FIG. 5C. This could be performed at a second time interval. For example, assuming that the user has not moved their head or changed their gaze, the optimum volume rendering strategy could be worked from the inside (e.g., small square first) to the outside (e.g., large square second). The second portion 511 is located in outer portions of the image 509. Therefore, timing can be coupled with location to determine optimized volume rendering strategies.

Figure 6A:
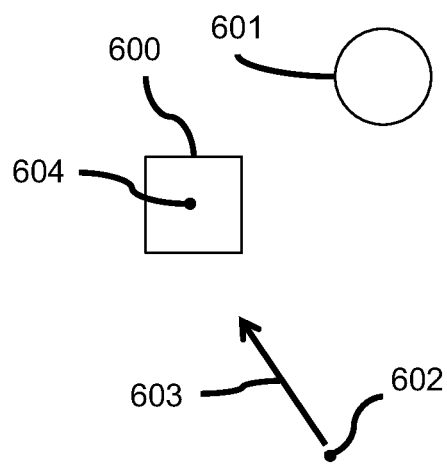
FIG. 6A is a top down view at a first time point showing a first viewing point, a first viewing angle and a first convergence point.

FIG. 6A is a top down view at a first time point showing a first viewing point, a first viewing angle and a first convergence point. 600 illustrates a first segmented object.

601 illustrates a second segmented object. 602 illustrates a viewing location. 603 illustrates a first viewing angle. 604 illustrates a first convergence point.

Figure 6B:
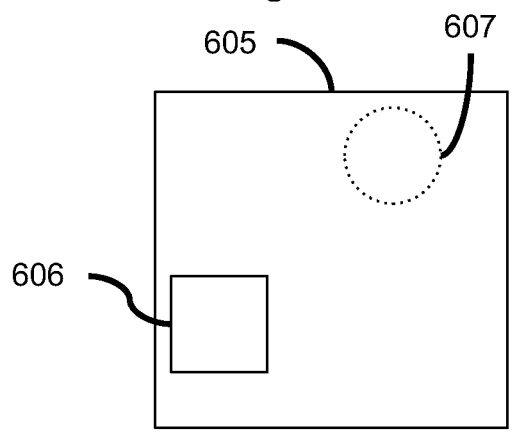
FIG. 6B illustrates a rendered image from FIG. 6A displayed at the first time point.

FIG. 6B illustrates a rendered image from FIG. 6A displayed at the first time point. 605 illustrates a rendered image from FIG. 6A. A prioritization scheme is utilized. Since the convergence point 604 is focused on object 600, as shown in FIG. 6A, object 600 will be displayed with its optimized rendering scheme, which in this example is voxel rendering. 606 illustrates an image of the first segmented object 600 from FIG. 6A, which utilizes an optimized volume rendering strategy and is displayed in the most optimized fashion possible. Assume that the optimized volume rendering strategy for object 600 from FIG. 6A is voxel rendering. Assuming this, then object 600 in FIG. 6A will be rendered using a voxel rendering strategy. This data can be stored for later use, see FIG. 6E below. At this juncture, the other portions of the volume may or may not be rendered with their most optimum type of rendering. If the processor is fast enough to display all objects with their most optimum type of rendering, then each object (e.g., segmented structure) will be rendered with its most optimum type of rendering. If not, then some objects in the volume will be given a lower tiered rendering strategy. In this time point, object 601 is given a lower tiered rendering strategy. The #1 preferred rendering type for object 601 is voxel rendering; however, since the processor is not fast enough to display object 601 with the #1 preferred rendering type (e.g., voxel rendering), object 601 is therefore rendered as a lower preference type of rendering (e.g., point cloud). 607 illustrates the second segmented object from FIG. 1A, which utilizes a non-optimized volume rendering strategy. This example uses a single view point and does not account for user head movement.

Figure 6C:
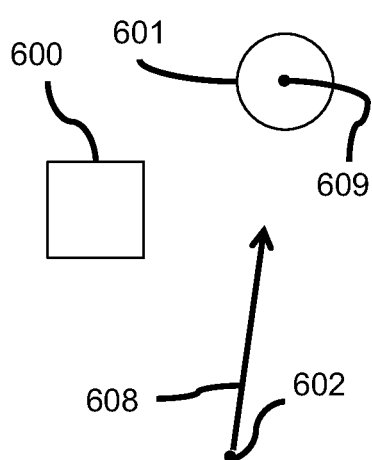

FIG. 6C is a top down view at a second time point showing a first viewing point, a second viewing angle and a second convergence point. 600 illustrates the first segmented object. 601 illustrates the second segmented object. 602 illustrates the viewing location. 608 illustrates a second viewing angle. Note that this is different from the first viewing angle 603 in FIG. 6A. 609 illustrates a second convergence point. Note that this is different from the first convergence point 604 in FIG. 6A. In this example, the viewing location does not change (e.g., in a HDU with head tracking, no head movement occurs).

Figure 6D:
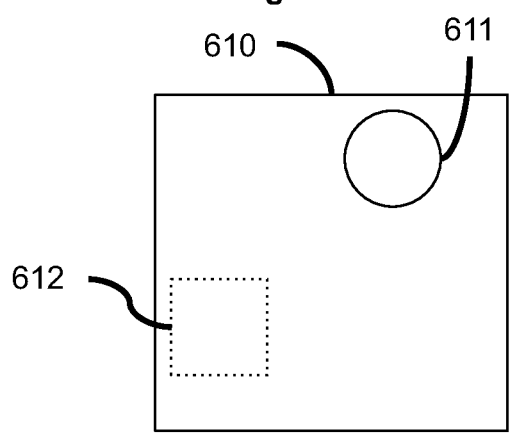

FIG. 6D illustrates a rendered image from FIG. 6C displayed at a second time point. 610 illustrates a rendered image from FIG. 6C. A prioritization scheme is utilized. Since the convergence point 109 is focused on object 601, as shown in FIG. 6C, object 601 will be displayed with its optimized rendering scheme, which in this example is voxel rendering. 611 illustrates an image of the first segmented object 601 from FIG. 6C, which utilizes an optimized volume rendering strategy and is displayed in the most optimized fashion possible. Assume that the optimized volume rendering strategy for object 601 from FIG. 6C is voxel rendering. Assuming this, then object 601 in FIG. 6C will be rendered using a voxel rendering strategy. At this juncture, the other portions of the volume may or may not be rendered with their most optimum type of rendering. If the processor is fast enough to display all objects with their most optimum type of rendering, then each object (e.g., segmented structure) will be rendered with its most optimum type of rendering. If not, then some objects in the volume will be given a lower tiered rendering strategy. In this time point, object 600 is given a lower tiered rendering strategy. The #1 preferred rendering type for object 600 is voxel rendering; however, since the processor is not fast enough to display object 600 with the #1 preferred rendering type (e.g., voxel rendering), object 600 is therefore rendered as a lower preference type of rendering (e.g., point cloud). 612 illustrates the second segmented object from FIG. 1A, which utilizes an non-optimized volume rendering strategy. This example uses a single view point and does not account for user head movement. Thus, the rendering that occurs for objects 600 and 601 a first time point can be different from the rendering that occurs for objects 600 and 601 at a second time point. In this example, the viewing angle and the convergence point determine the object (portion of the volume) that undergoes the first type (preferred type) or rendering.

Figure 6E:
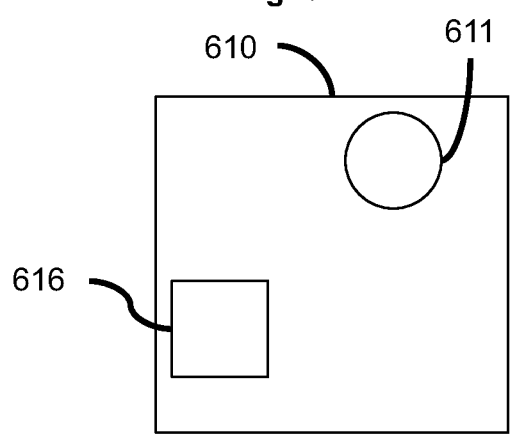

FIG. 6E illustrates a rendered image from FIG. 6C displayed at a second time point. 613 illustrates a rendered image from FIG. 6C. A prioritization scheme is utilized. Since the convergence point 109 is focused on object 601, as shown in FIG. 6C, object 601 will be displayed with its optimized rendering scheme, which in this example is voxel rendering. 611 illustrates an image of the first segmented object 601 from FIG. 6C, which utilizes an optimized volume rendering strategy and is displayed in the most optimized fashion possible. Assume that the optimized volume rendering strategy for object 601 from FIG. 6C is voxel rendering. Assuming this, then object 601 in FIG. 6C will be rendered using a voxel rendering strategy. At this juncture, the other portions of the volume may or may not be rendered with their most optimum type of rendering. If the processor is fast enough to display all objects with their most optimum type of rendering, then each object (e.g., segmented structure) will be rendered with its most optimum type of rendering. If not, then some objects in the volume will be given a lower tiered rendering strategy. In this time point, object 600 is given a lower tiered rendering strategy. However, in this example, since the view point did not move, object 600 did not move, and object 600 has already been rendered with its most optimum type of rendering (i.e., stored from FIG. 6A, see above), the object 600 can be displayed with an optimized volume rendering strategy without having to perform any rendering. This is useful because it improves image quality while also reducing processing requirements. This example uses a single viewpoint and does not account for user head movement. Thus, optimized rendering can occur for objects 600 and 601 at a second time point by performing optimized rendering for object 601 at the second time point and displaying object 600 in an optimized fashion (optimized volume rendering was performed at a previous time point).

Figure 7A:
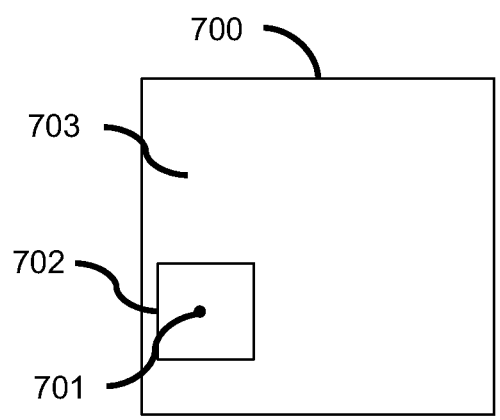
FIG. 7A illustrates dividing at a first time point the field of view into a first portion and at least one additional portion by eye tracking metrics.

FIG. 7A illustrates dividing at a first time point the field of view into a first portion and at least one additional portion by eye tracking metrics. This method involves the performing eye tracking to determine where the user is looking at a given time point. Then performing a preferred type of rendering in the region in close proximity to where the user is looking. And, in regions far away from where the user is looking, a different type of rendering can be performed. This can be displayed in the methods disclosed in U.S. patent application Ser. No. 16/893,291. 700 illustrates an image at a first time point. 701 illustrates a first convergence point. 702 illustrates a first portion of the image at a first time point, which surrounds the first convergence point 701. 703 illustrates a second portion of the image at a first time point.

Figure 7B:
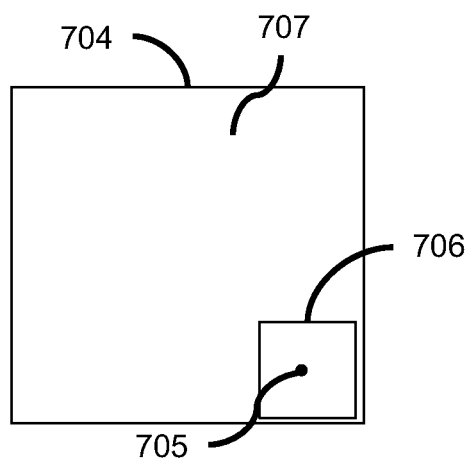
FIG. 7B illustrates dividing at a second time point the field of view into a first portion and at least one additional portion by eye tracking metrics.

FIG. 7B illustrates dividing at a second time point the field of view into a first portion and at least one additional portion by eye tracking metrics. This method involves the performing eye tracking to determine where the user is looking at a given time point. Then performing a preferred type of rendering in the region in close proximity to where the user is looking. And, in regions far away from where the user is looking, a different type of rendering can be performed. This can be displayed in the methods disclosed in U.S. patent application Ser. No. 16/893,291. 704 illustrates an image at a second time point. 705 illustrates a second convergence point. 706 illustrates a first portion of the image at a second time point, which surrounds the second convergence point 705. 707 illustrates a second portion of the image at a second time point.

Figure 7C:
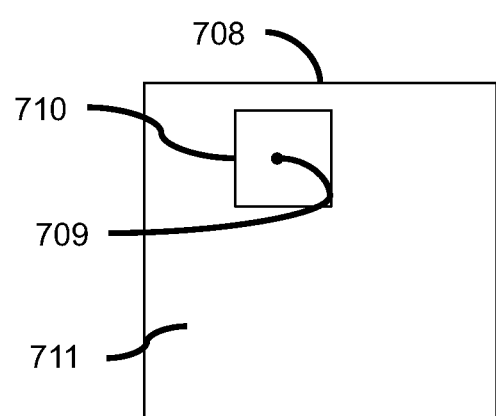
FIG. 7C illustrates dividing at a third time point the field of view into a first portion and at least one additional portion by eye tracking metrics.

FIG. 7C illustrates dividing at a third time point the field of view into a first portion and at least one additional portion by eye tracking metrics. This method involves the performing eye tracking to determine where the user is looking at a given time point. Then performing a preferred type of rendering in the region in close proximity to where the user is looking. And, in regions far away from where the user is looking, a different type of rendering can be performed. This can be displayed in the methods disclosed in U.S. patent application Ser. No. 16/893,291. 708 illustrates an image at a third time point. 709 illustrates a third convergence point. 710 illustrates a first portion of the image at a third time point, which surrounds the third convergence point 709. 711 illustrates a second portion of the image at a third time point.

Figure 7D:
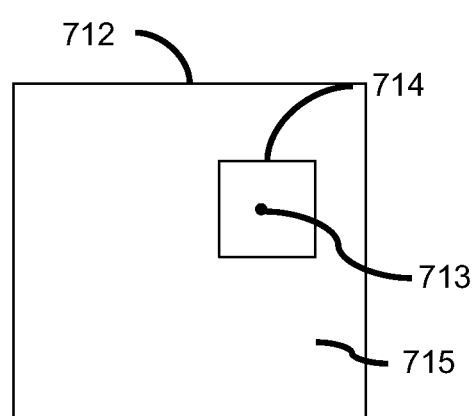
FIG. 7D illustrates dividing at a fourth time point the field of view into a first portion and at least one additional portion by eye tracking metrics.

FIG. 7D illustrates dividing at a fourth time point the field of view into a first portion and at least one additional portion by eye tracking metrics. This method involves the performing eye tracking to determine where the user is looking at a given time point. Then performing a preferred type of rendering in the region in close proximity to where the user is looking. And, in regions far away from where the user is looking, a different type of rendering can be performed. This can be displayed in the methods disclosed in U.S. patent application Ser. No. 16/893,291. 712 illustrates an image at a fourth time point. 713 illustrates a fourth convergence point. 714 illustrates a first portion of the image at a fourth time point, which surrounds the fourth convergence point 713. 715 illustrates a second portion of the image at a fourth time point.

Figure 8A:
FIG. 8A illustrates a volume rendered image with the whole image rendered as voxels.

FIG. 8A illustrates a volume rendered image with the whole image rendered as voxels. 800 illustrates the volume rendered image of cerebrovasculature. Note that the entire image 800 is rendered as voxels. Note that non-vascular structures have been filtered (i.e., subtracted). Note that light shading has been performed. Note that the voxels are small enough so that the user does not get the stair-step (or cube-like) appearance. Assuming that the processor has the capability to render the entire volume sufficiently fast (e.g., 60 Hz), then it would be preferred to have the entire volume be displayed with the preferred rendering strategy.

Figure 8B:
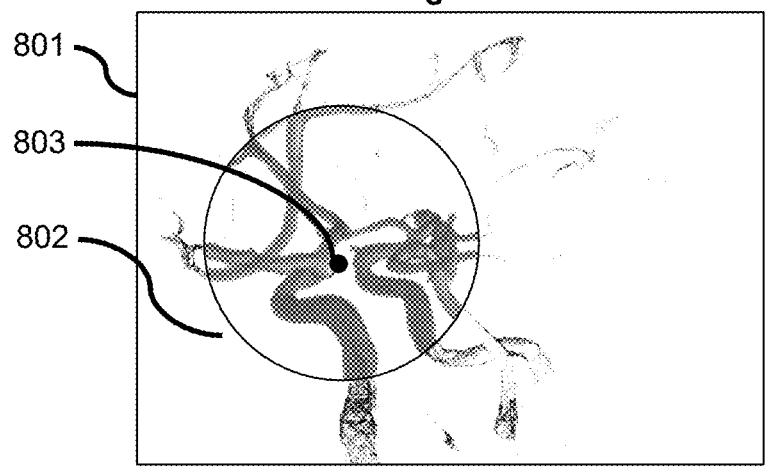
FIG. 8B illustrates a volume rendered image with a portion of the image where the user is looking rendered as voxels and a portion of the image rendered with point clouds.

FIG. 8B illustrates a volume rendered image with a portion of the image where the user is looking rendered as voxels and a portion of the image rendered with point clouds. 801 illustrates the portion of the image that is rendered as point clouds. Note that the sampling is sparse. 802 illustrates the portion of the image that is rendered as voxels. This volume 802 is defined by the convergence point of the user and a radius (e.g., 5 cm). 803 illustrates the fixation location of the user at this time point. In this example, the fixation location determines the first portion of the volume 801 that is rendered as a point cloud and the second portion of the volume 802 that is rendered as voxels.

Figure 8C:
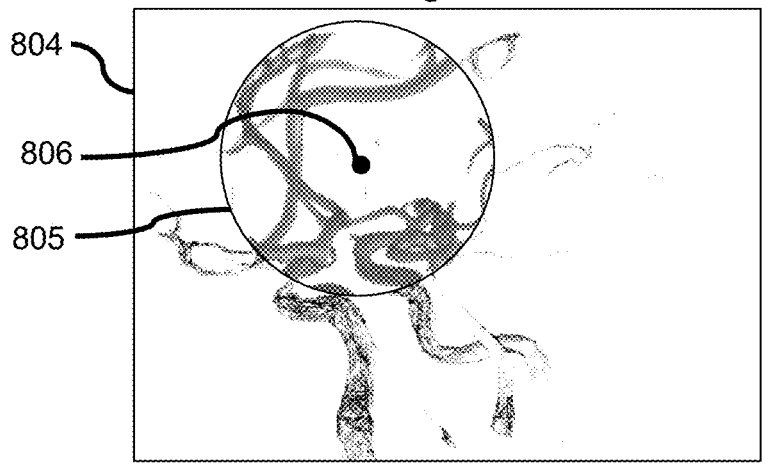
FIG. 8C illustrates a volume rendered image with a portion of the image where the user is looking rendered as voxels and a portion of the image rendered with point clouds.

FIG. 8C illustrates a volume rendered image with a portion of the image where the user is looking rendered as voxels and a portion of the image rendered with point clouds. 804 illustrates the portion of the image that is rendered as point clouds. Note that the sampling is sparse. 805 illustrates the portion of the image that is rendered as voxels. This volume 805 is defined by the convergence point of the user and a radius (e.g., 5 cm). 806 illustrates the fixation location of the user at this time point. In this example, the fixation location determines the first portion of the volume 804 that is rendered as a point cloud and the second portion of the volume 805 that is rendered as voxels. This is useful because it provides high quality rendering at the location where the user is looking at all times, but overall speeds rendering.

Figure 9:
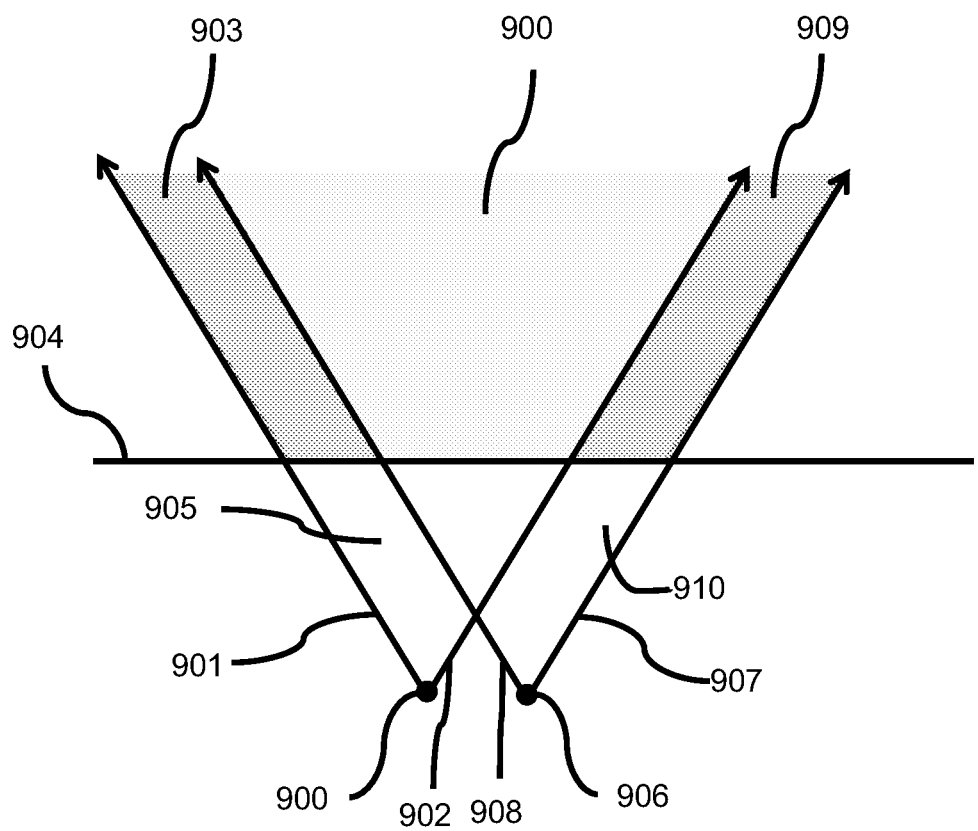
FIG. 9 illustrates a method of dividing the volume into two portions.

FIG. 9 illustrates a method of dividing the volume into two portions. 900 illustrates a left eye viewpoint. 901 illustrates the lateral boundary of the left eye field of view. 902 illustrates the medial boundary of the left eye field of view. 903 illustrates a medium gray region, which illustrates a rendered portion of the volume of interest seen by the left eye. 904 illustrates a geometric boundary, which is used to cause filtering on one side of the boundary. Note that portions of the volume of interest on the side of the geometric boundary closest to the left eye viewpoint 900 and right eye viewpoint 906 can be filtered (e.g., subtracted). This is discussed in U.S. Pat. No. 8,384,771 METHOD AND APPARATUS FOR THREE DIMENSIONAL VIEWING OF IMAGES and U.S. Provisional Patent Application 60/877,931 for details on geometric boundary method. 905 illustrates a white region in between the lateral boundary of the left eye field of view 901 and the medial boundary of the right eye field of view 902, which illustrates the non-rendered portion of the volume of interest. 906 illustrates a right eye viewpoint. 907 illustrates the lateral boundary of the right eye field of view. 908 illustrates the medial boundary of the right eye field of view. 909 illustrates a medium gray region, which illustrates a rendered portion of the volume of interest seen by the right eye. 910 illustrates a white region in between the lateral boundary of the right eye field of view 907 and the medial boundary of the right eye field of view 908, which illustrates the non-rendered portion of the volume of interest. 911 illustrates a light gray region, which illustrates a portion of the volume of interest seen by both the right eye and left eye. Note that the human eye has higher resolution in the portions of the volume of interest seen by both eyes. This diagram illustrates wherein a first portion of the volume of interest (e.g., light gray region 911) can be rendered with a first type of rendering (e.g., optimized rendering, such as voxel rendering) and a second portion of the volume of interest (e.g., medium gray region 903 and medium gray region 909) can be rendered with a second type of rendering (non-optimized rendering, such as point cloud rendering).

Figure 10A:
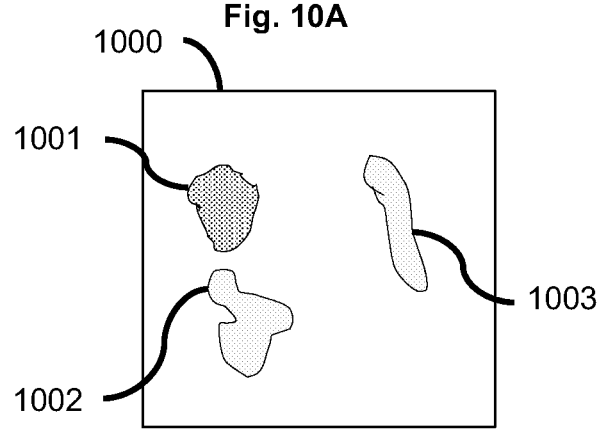
FIG. 10A illustrates an example wherein an artificial intelligence algorithm determines how to divide the volume for a tandem volume rendering strategy at a first time point.

FIG. 10A illustrates an example wherein an artificial intelligence algorithm determines how to divide the volume for a tandem volume rendering strategy at a first time point. 1000 illustrates the rendered image at a first time point. 1001 illustrates a first object, which is directed by a computer algorithm (e.g., artificial intelligence) to be rendered with an optimized volume rendering strategy. 1002 illustrates a second object, which is directed by a computer algorithm (e.g., artificial intelligence) to be rendered with a non-optimized volume rendering strategy. 1003 illustrates a third object, which is directed by a computer algorithm (e.g., artificial intelligence) to be rendered with a non-optimized volume rendering strategy. In this example, an artificial intelligence algorithm determines how to divide the volume at a first time point. Thus, the volume containing three items can be divided. Next, each divided portion of the volume must be assigned a particular type of rendering. In this example, the type of rendering assigned is via artificial intelligence. A first portion of the volume can be displayed with a first type of rendering. An additional portion of the volume can be displayed with a second type of rendering.

Figure 10B:
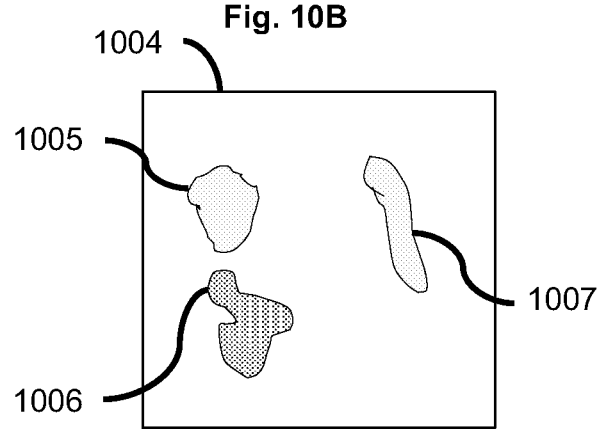
FIG. 10B illustrates an example wherein an artificial intelligence algorithm determines how to divide the volume for a tandem volume rendering" volume rendering strategy at a second time point.

FIG. 10B illustrates an example wherein an artificial intelligence algorithm determines how to divide the volume for a tandem volume rendering" volume rendering strategy at a second time point. 1004 illustrates the rendered image at a second time point. 1005 illustrates a first object, which is directed by a computer algorithm (e.g., artificial intelligence) to be rendered with a non-optimized volume rendering strategy. 1006 illustrates a second object, which is directed by a computer algorithm (e.g., artificial intelligence) to be rendered with an optimized volume rendering strategy. 1007 illustrates a third object, which is directed by a computer algorithm (e.g., artificial intelligence) to be rendered with a non-optimized volume rendering strategy. In this example, an artificial intelligence algorithm determines how to divide the volume at a second time point. Thus, the volume containing three items can be divided. Next, each divided portion of the volume must be assigned a particular type of rendering. In this example, the type of rendering assigned is via artificial intelligence.

A first portion of the volume can be displayed with a first type of rendering. An additional portion of the volume can be displayed with a second type of rendering.

Figure 10C:
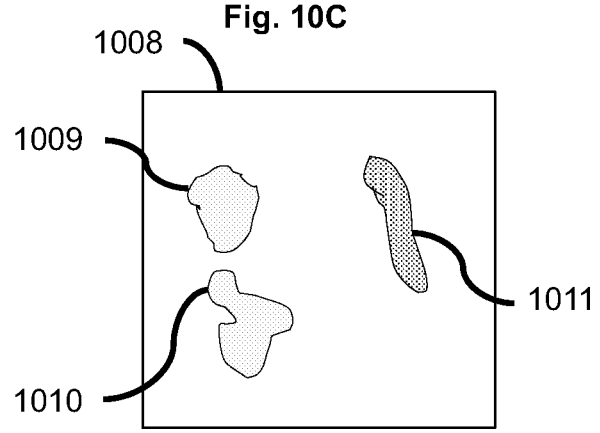
FIG. 10C illustrates an example wherein an artificial intelligence algorithm determines how to divide the volume for a tandem volume rendering strategy at a third time point.

FIG. 10C illustrates an example wherein an artificial intelligence algorithm determines how to divide the volume for a tandem volume rendering strategy at a third time point. 1008 illustrates the rendered image at a third time point. 1009 illustrates a first object, which is directed by a computer algorithm (e.g., artificial intelligence) to be rendered with a non-optimized volume rendering strategy. 1010 illustrates a second object, which is directed by a computer algorithm (e.g., artificial intelligence) to be rendered with a non-optimized volume rendering strategy. 1011 illustrates a third object, which is directed by a computer algorithm (e.g., artificial intelligence) to be rendered with an optimized volume rendering strategy. In this example, an artificial intelligence algorithm determines how to divide the volume at a third time point. Thus, the volume containing three items can be divided. Next, each divided portion of the volume must be assigned a particular type of rendering. In this example, the type of rendering assigned is via artificial intelligence. A first portion of the volume can be displayed with a first type of rendering. An additional portion of the volume can be displayed with a second type of rendering.

FIG. 11A illustrates a first viewing perspective looking at a cluster of microcalcifications wherein some of the microcalcifications are determined to be benign and some of the microcalcifications are determined to be suspicious. 1100 illustrates a cluster of 16 microcalcifications, of which 3 are determined (by an artificial intelligence algorithm) to be suspicious and 13 are determined (by an artificial intelligence algorithm) to be benign. 1101 illustrates a viewing perspective. 1102 illustrates a first suspicious microcalcification. Note that from the viewing perspective 1101, the first suspicious microcalcification 1102 will be partially hidden by a first benign microcalcification 1103, a second benign microcalcification 1104 and a third benign microcalcification 1105. 1106 illustrates a second suspicious microcalcification. Note that from the viewing perspective 1101, the second suspicious microcalcification 1106 is partially obscured by a fourth benign microcalcification 1107 and a fifth benign microcalcification 1108. 1109 illustrates a third suspicious microcalcification. Note that from the viewing perspective 1101, the third suspicious microcalcification 1109 is partially obscured by a sixth benign microcalcification 1110 and also note that there is a seventh benign microcalcification 1111 located behind it, which could also impair visualization of the third suspicious microcalcification 1109. Note that 1112 represents an eighth benign microcalcification, which is not overlapping with any of the suspicious microcalcifications from viewing perspective 1101. Note that 1113 represents an ninth benign microcalcification, which is not overlapping with any of the suspicious microcalcifications from viewing perspective 1101. Note that 1114 represents an tenth benign microcalcification, which is not overlapping with any of the suspicious microcalcifications from viewing perspective 1101. Note that 1115 represents an eleventh benign microcalcification, which is not overlapping with any of the suspicious microcalcifications from viewing perspective 1101. Note that 1116 represents an twelfth benign microcalcification, which is not overlapping with any of the suspicious microcalcifications from viewing perspective 1101. Note that 1117 represents an thirteenth benign microcalcification, which is not overlapping with any of the suspicious microcalcifications from viewing perspective 1101.

FIG. 11B illustrates dividing the volume of microcalcifications into a first portion. In this example, a computer monitor 1118 displays only the first portion of the volume. In this example, the first portion includes the first suspicious microcalcification 1102, the second suspicious microcalcification 1106 and the third suspicious microcalcification 1109. These three suspicious microcalcifications can be given the optimized volume rendering strategy (e.g., voxel rendering with a high frame rate of 120 Hz). In this example, they are displayed alone (i.e., without the second portion of the volume, as discussed below).

FIG. 11C illustrates dividing the volume of microcalcifications into a second portion. In this example, a computer monitor 1119 displays only the second portion of the volume. In this example, the second portion includes a first benign microcalcification 1103, a second benign microcalcification 1104, a third benign microcalcification 1105, a fourth benign microcalcification 1107, a fifth benign microcalcification 1108, a sixth benign microcalcification 1110, a seventh benign microcalcification 1111, an eighth benign microcalcification 1112, a ninth benign microcalcification 1113, a tenth benign microcalcification 1114, an eleventh benign microcalcification 1115, a twelfth benign microcalcification 1116, and a thirteenth benign microcalcification 1117.

FIG. 12A illustrates a volume containing four objects with each object having a unique set of imaging features. 1200 illustrates the volume. 1201 illustrates a first object, which is oval shaped, smooth margins and homogeneous internal architecture. 1202 illustrates a second object, which is round shaped, smooth margins and heterogeneous internal architecture. 1203 illustrates a third object, which is oval shaped, spiculated margins and heterogeneous internal architecture. 1204 illustrates a fourth object, which is round shaped, spiculated margins and homogeneous internal architecture. These imaging features are examples. Examples of other imaging features of a segmented object include: shape (e.g., round shaped, irregular shaped, etc.); size (e.g., smaller than 1 $cm^3$, larger than 1 $cm^3$, etc.); margins (e.g., smooth, ill-defined, spiculated, etc.); internal architecture (e.g., homogeneous, heterogeneous, etc.); and, prioritization level (as described in U.S. Pat. No. 10,766,989). In this example, the processing speed is sufficient to perform optimized (e.g., voxel rendering) of each object within the imaging volume in near real time.

FIG. 12B illustrates a volume containing four objects with each object having a unique set of imaging features wherein the volume is divided into a first portion based on the imaging feature of round shape and a second portion based on oval shape. 1205 illustrates the volume. 1206 illustrates a first object, which is oval shaped, smooth margins and homogeneous internal architecture, which is divided into the first portion based on the imaging feature of oval shape. 1207 illustrates a second object, which is round shaped, smooth margins and heterogeneous internal architecture, which is divided into the second portion based on the imaging feature of round shape. 1208 illustrates a third object, which is oval shaped, spiculated margins and heterogeneous internal architecture, which is divided into the first portion based on the imaging feature of oval shape. 1209 illustrates a fourth object, which is round shaped, spiculated margins and homogeneous internal architecture, which is divided into the second portion based on the imaging feature of round shape. Since the first object 1206 and the third object 1208 are both in the first portion of the volume, so they are rendered using an optimized rendering strategy (e.g., voxel rendering). Assume in this scenario that there is insufficient processing capabilities to render the second object 1207 and the fourth object 1209 in the optimized fashion. Since the second object 1207 and the fourth object 1209 are both in the second portion of the volume, they are rendered using a non-optimized rendering strategy (e.g., point cloud rendering, partial transparency rendering).

FIG. 12C illustrates a volume containing four objects with each object having a unique set of imaging features wherein the volume is divided into a first portion based on the imaging feature of smooth margins and a second portion based on spiculated margins. 1210 illustrates the volume. 1211 illustrates a first object, which is oval shaped, smooth margins and homogeneous internal architecture, which is divided into the second portion based on the imaging feature of smooth margins. 1212 illustrates a second object, which is round shaped, smooth margins and heterogeneous internal architecture, which is divided into the second portion based on the imaging feature of round shape. 1213 illustrates a third object, which is oval shaped, spiculated margins and heterogeneous internal architecture, which is divided into the first portion based on the imaging feature of spiculated margins. 1214 illustrates a fourth object, which is round shaped, spiculated margins and homogeneous internal architecture, which is divided into the first portion based on the imaging feature of spiculated margins. Since the third object 1213 and the fourth object 1214 are both in the first portion of the volume, so they are rendered using an optimized rendering strategy (e.g., voxel rendering). Assume in this scenario that there is insufficient processing capabilities to render the first object 1211 and the second object 1212 in the optimized fashion. Since the the first object 1211 and the second object 1212 are both in the second portion of the volume, they are rendered using a non-optimized rendering strategy (e.g., point cloud rendering, partial transparency rendering).

FIG. 12D illustrates a volume containing four objects with each object having a unique set of imaging features wherein the volume is divided into a first portion based on the imaging feature of heterogeneous internal architecture and a second portion based on homogeneous internal architecture. 1215 illustrates the volume. 1216 illustrates a first object, which is oval shaped, smooth margins and homogeneous internal architecture, which is divided into the second portion based on the imaging feature of homogeneous internal architecture. 1217 illustrates a second object, which is round shaped, smooth margins and heterogeneous internal architecture, which is divided into the first portion based on the imaging feature of heterogeneous internal architecture. 1218 illustrates a third object, which is oval shaped, spiculated margins and heterogeneous internal architecture, which is divided into the first portion based on the imaging feature of heterogeneous internal architecture. 1219 illustrates a fourth object, which is round shaped, spiculated margins and homogeneous internal architecture, which is divided into the second portion based on the imaging feature of homogeneous internal architecture. Since the second object 1217 and the third object 1218 are both in the first portion of the volume, so they are rendered using an optimized rendering strategy (e.g., voxel rendering). Assume in this scenario that there is insufficient processing capabilities to render the first object 1215 and the fourth object 1219 in the optimized fashion. Since the the first object 1215 and the fourth object 1219 are both in the second portion of the volume, they are rendered using a non-optimized rendering strategy (e.g., point cloud rendering, partial transparency rendering).

FIG. 12E illustrates a volume containing four objects with each object having a unique set of imaging features wherein the volume is divided into a first portion based on having the imaging feature of both spiculated margins and heterogeneous internal architecture and a second portion will include all segmented structures not meeting criteria for the first portion. 1220 illustrates the volume. 1221 illustrates a first object, which is oval shaped, smooth margins and homogeneous internal architecture, which is divided into the second portion based on not meeting criteria for the first portion. 1222 illustrates a second object, which is round shaped, smooth margins and heterogeneous internal architecture, which is divided into the second portion based on not meeting criteria for the first portion. 1223 illustrates a third object, which is oval shaped, spiculated margins and heterogeneous internal architecture, which is divided into the first portion based on having both spiculated margins and heterogeneous internal architecture. 1224 illustrates a fourth object, which is round shaped, spiculated margins and homogeneous internal architecture, which is divided into the second portion based on not meeting criteria for the first portion. Since the third object 1223 is in the first portion of the volume, it is rendered using an optimized rendering strategy (e.g., voxel rendering). Assume in this scenario that there is insufficient processing capabilities to render the first object 1221, the second object 1222 and the fourth object 1224 in the optimized fashion. Since the the first object 1221, the second object 1222 and the fourth object 1224 are all in the second portion of the volume, they are rendered using a non-optimized rendering strategy (e.g., point cloud rendering, partial transparency rendering).

FIG. 13 illustrates a text box describing factors used to determine the preferred type of rendering. First, it should be noted that different types of rendering can be used to optimize visualization of different types of structures. For example, subcutaneous fat is usually of little importance to the radiologist. Therefore, it can be rendered as a point cloud with sparse sampling. Other structures (e.g., a tumor) would be of great importance and it would be desired to be viewed in its most optimized fashion (e.g., voxel rendering and prioritized volume rendering per U.S. Pat. No. 10,776,989. Text box 1300 illustrates a variety of factors, which can be used to determine the preferred type of rendering.

An imaging feature (e.g., property of a segmented object) can be utilized to determine the preferred type of rendering.

Examples of imaging features include, but are not limited to the following: shape (e.g., round shaped, irregular shaped, etc.); size (e.g., smaller than 1 cm$^3$, larger than 1 cm$^3$, etc.); margins (e.g., smooth, ill-defined, spiculated, etc.); internal architecture (e.g., homogeneous, heterogeneous, etc.); and, prioritization (as described in U.S. Pat. No. 10,766,989). For example, a bone may be rendered as a polygon mesh.

Next, the results from analysis methods (e.g., Artificial intelligence (AI)) can be used to determine the preferred type of rendering for a segmented object. For example, if an AI algorithm determines that a segmented object is benign, then a first type of rendering can be performed (e.g., point cloud rendering). On the other hand, if an AI algorithm determines that a segmented object is malignant, then a second type of rendering is performed (e.g., voxel rendering).

Next, the timing features can be used alone or in combination with any other factor discussed herein. For example, it be determined that a first view of the image may be given a low-resolution view (e.g., a first type of rendering) for the first N seconds and a high-resolution view thereafter (e.g., a second type of rendering).

Next, the desired field of view can be used to determine the type of rendering. For example, large field of view may cause a first portion of the volume (e.g., structure located in the periphery) to have a first type of rendering (e.g., point cloud rendering) and a second structure (e.g., structure located in the central component) to have a second type of rendering (e.g., voxel rendering).

Next, computer processing capabilities may also determine the preferred type of rendering. For example, a first computer processing capability setup may divide the volume into a first portion of the image rendered at a first preferred rate (e.g., 120 Hz) and a second portion rendered at a second rate (e.g., 60 Hz). Additionally, a second computer processing capability setup may divide the volume into a first portion of the image rendered at a first preferred rate (e.g., 60 Hz) and a second portion rendered at a second rate (e.g., 30 Hz). The computer(s) and/or processing speed available can be used as a factor in determining the preferred type of rendering. In other words, a first computer system can have a first set of tandem rendering. A second computer can have a second set of tandem rendering. Note that computers can also be used in conjunction with one another (e.g., a first computer performs rendering of the first portion, second computer performs rendering of the second portion, etc.).

FIG. 14 illustrates preferred rendering schemes for different segmented structures. Each structure in the volume may have a different preference in rendering. Two examples are provided. First is in the field of medical imaging and the example discussed is a vascular structure. Second is in the field of terrain representation (e.g., LiDAR generated dataset).

Text box 1400 illustrates examples of ways a segmented structure (e.g., vascular structure) can be rendered (ordered by user preference). For a vascular structure, the following preference can be established. The #1 preferred option is to model the volume as very small (sub-mm isotropic) voxels and perform false light to achieve shading. A first rationale is that if user zooms in, then the voxels will not appear cube-like. In addition, to further prevent the cube-like appearance, voxel manipulation can be performed during zooming in, which can be performed as discussed in U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION. A second rationale is to use false light with shading to provide an improved monocular depth cue. The #2 preferred option is to use larger voxels (e.g., 1 mm isotropic). The rationale is that this minimally degrades image quality. The #3 preferred option is to model the volume as a point cloud. The rationale is that this provides very fast rendering. Thus a first segmented structure can have its own order of preference on types of rendering. And, a second segmented structure can have its own order of preference on types of rendering.

Text box 1401 illustrates examples of ways a segmented structure (e.g., terrain) can be rendered (ordered by user preference). The #1 preferred option would be to model the volume as very small voxels. The #2 option would be to model the volume as a polygon mesh. The #3 option would be to model the volume as a point cloud.

Figure 15:
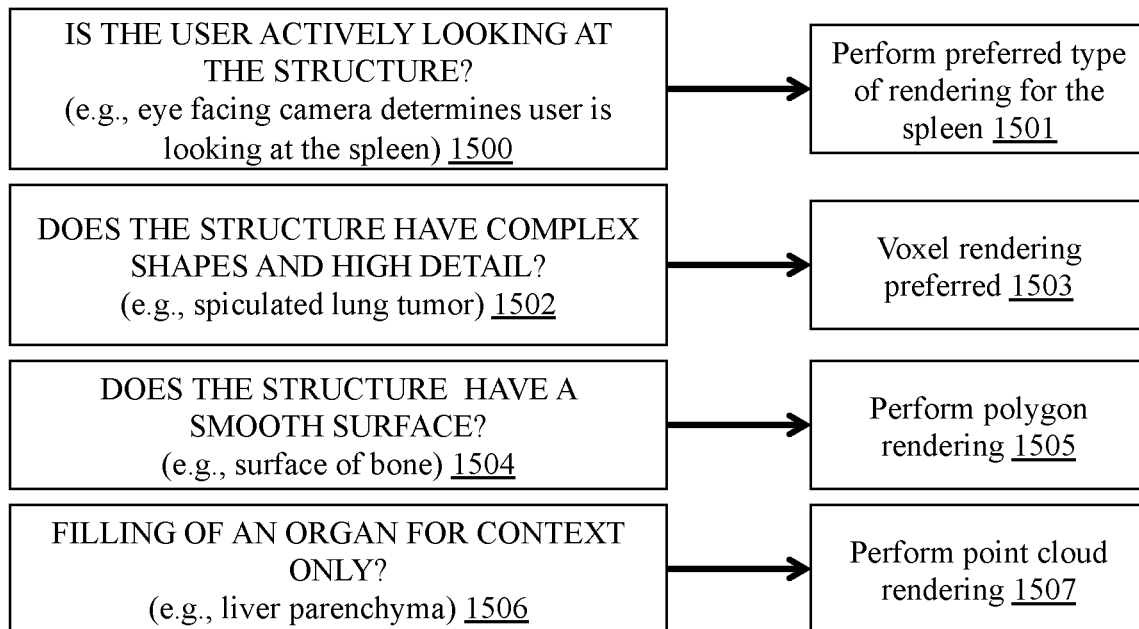
FIG. 15 illustrates a text box showing example factors that can be used in determining preferred type of rendering for structures within the volume.

FIG. 15 illustrates a text box showing example factors that can be used in determining preferred type of rendering for structures within the volume. Text box 1500 illustrates a question of "is the user actively looking at the structure?" This question can be answered by using an eye facing camera and determining that a user is looking at the spleen. Text box 1501 illustrates an answer to this question, which states "perform preferred type of rendering for the spleen". This question and answer should give the reader context as to when the preferred type of rendering should be utilized. Text box 1502 illustrates the question of "does the structure have complex shapes and high detail?" For example, is the structure of a spiculated lung tumor? These types of questions can be programmed into an algorithm in determining the preferred type of rendering. Text box 1503 illustrates the answer to this question, which states "voxel rendering preferred." Text box 1504 illustrates the question of "does the structure have a smooth surface?" For example, does the structure involve the surface of the bone? If so, as illustrated in text box 1505, the preferred type of rendering may be polygon mesh rendering. Text box 1506 illustrates the question of "filling in of an organ for context only?" For example, the inner portion of the liver including the parenchyma is the segmented object in discussion. Text box 1507 illustrates an answer, which states "perform point cloud rendering".

FIG. 16 illustrates a text box conventional and advanced types of rendering. Text box 1600 describes example types of rendering. A first advanced rendering method is tandem rendering is to use a first type of conventional rendering for a first portion of the volume and a second type of rendering for a second portion of the volume. For example, a first portion of the volume (e.g., subcutaneous fat) can be rendered with a first type of rendering (e.g., point cloud rendering with sparse selection) and a second portion of the volume (e.g., bone) can be rendered with a second type of rendering (e.g., voxel rendering). Next, a set of advanced rendering methods will be discussed.

The second advanced rendering method is transparent rendering. Some 3D datasets (e.g., MRI scans and CT Scans) can be very large and very complex. In order to present the data to the user so the user can view exactly the structure of interest effectively, some of the structures of non-interest can be rendered transparent so that the structures of interest can be better visualized without suffering from overlap. This technique has been previously described in U.S. Pat. No. 8,384,771, METHOD AND APPARATUS FOR THREE-DIMENSIONAL VIEWING OF IMAGES. This patent presents an algorithm on when to use this type of rendering. This will be discussed more in subsequent figures.

The third advanced rendering method is partial image rendering. A texture map of a first rendered image will be generated. It will then be re-used on a subsequent similar image (e.g., the user makes a small turn of his/her head, looks a slightly different direction). This will be discussed in subsequent figures.

The fourth advanced rendering method is called preemptive volume rendering will also be discussed wherein a set of rendered images are performed before a user looks at a particular convergence point or moved his/her head to a particular viewing position/orientation. This strategy speeds up rendering rates by utilizing preemptively rendered images. Within this fourth advanced rendering method are three sub-types. The first subtype is called predictive-type preemptive volume rendering. The second subtype is called localized-type preemptive volume rendering. The third subtype is called global-type preemptive volume rendering. These will be discussed in subsequent figures.

The fifth advanced rendering method is called recalled volume rendering. In this type of rendering, the previously rendered images are stored along with the important data used to render the image. For example, if a left eye image was rendered using a left eye view point, left eye viewing angle and volume of interest, then the left eye image would be stored along with a left eye view point, left eye viewing angle and volume of interest. The data could be stored in a file (e.g., look up table). Then, when the left eye view point, left eye viewing angle and volume of interest are encountered, the left eye image will be displayed by recalling the file and the left eye image will not have to be re-rendered. In other words, recalled volume rendering is wherein the set of rendered images is stored (e.g., if D3D type rendering is performed on a large dataset per U.S. Pat. No. 8,384,771, METHOD AND APPARATUS FOR THREE-DIMENSIONAL VIEWING OF IMAGES and U.S. Pat. No. 9,349,183, METHOD AND APPARATUS FOR THREE DIMENSIONAL VIEWING OF IMAGES). In other words, if a left eye image is rendered for a convergence point, volume of interest, head position, field of view width and height and all other factors, that left eye image can be saved. Then, if the same convergence point, same volume of interest (e.g., same filtering settings, same display settings), same head position, same field of view width and height are encountered at a subsequent time point, then the previously rendered left eye image can be recalled and displayed. This serves to speed up the display process.

FIG. 17A illustrates how three objects are rendered at a first time point. There is a table showing the segmented structures, properties of segmented structures and preferred type of rendering. The top row of the table illustrates object #1, which has a volume of 1.05 cm$^3$ is round and has the preferred rendering (in descending order) of voxel rendering, polygon mesh rendering and point cloud rendering. The middle row of the table illustrates object #2, which has a volume of 2.01 cm$^3$ is irregular and spiculated and has the preferred rendering (in descending order) of voxxel rendering, polygon mesh rendering and point cloud rendering. The bottom row of the table illustrates object #3, which has a volume of 3.96 cm$^3$ is oval has the preferred rendering (in descending order) of voxel rendering, polygon mesh rendering and point cloud rendering. Note in this example, objects #1, #2 an #3 have the same preferred rendering preferences; however, it is possible that different objects have different order of preference of type of rendering. This rendering scheme could be performed due to the fact that at the second time point, the user is looking at object #1 and therefore object #1 needs to be optimized. The remaining objects do not need to be optimized. Objects #2 and #3 are given sub-optimal rendering as polygon mesh. The three different objects are rendered in a certain way at a first time point. Namely, Object #1 is a small object and is rendered as voxel rendering. Objects #2 and #3 are rendered as polygon mesh. Thus, at a given time point a first portions of the volume can be rendered with a first type of rendering and at least one other portion of the volume can be rendered with at least one additional type of rendering.

FIG. 17B illustrates tandem rendering of three objects at a second time point, which is called tandem dynamic rendering. There is a table showing the segmented structures, properties of segmented structures and preferred type of rendering. The top row of the table illustrates object #1, which has a volume of 1.05 cm$^3$ is round and has the preferred rendering (in descending order) of voxel rendering, polygon mesh rendering and point cloud rendering. The middle row of the table illustrates object #2, which has a volume of 2.01 cm$^3$ is irregular and spiculated and has the preferred rendering (in descending order) of voxel rendering, polygon mesh rendering and point cloud rendering. The bottom row of the table illustrates object #3, which has a volume of 3.96 cm$^3$ is oval has the preferred rendering (in descending order) of voxel rendering, polygon mesh rendering and point cloud rendering. Note in this example, objects #1, #2 an #3 have the same preferred rendering preferences; however, it is possible that different objects have different order of preference of type of rendering. The three different objects are rendered in a certain way at a second time point. Namely, Object #1 is a small object and is rendered as a point cloud. Objects #2 is rendered with voxels. Object #3 is rendered as a point cloud. This rendering scheme could be performed due to the fact that at the second time point, the user is looking at object #2 and therefore object #2 needs to be optimized. The remaining objects do not need to be optimized. Objects #1 and #3 are given sub-optimal rendering as point clouds. Thus, a first portion of the volume (e.g., Object #1 stone in bladder) can be rendered with a first type of rendering (e.g., voxel rendering) at a first time point and a second type of rendering (e.g., point cloud) at a subsequent time point. Thus, the type of rendering selected can change in a dynamic fashion to keep up with the refresh rate (e.g., 60 Hz) of the display.

Figure 18:
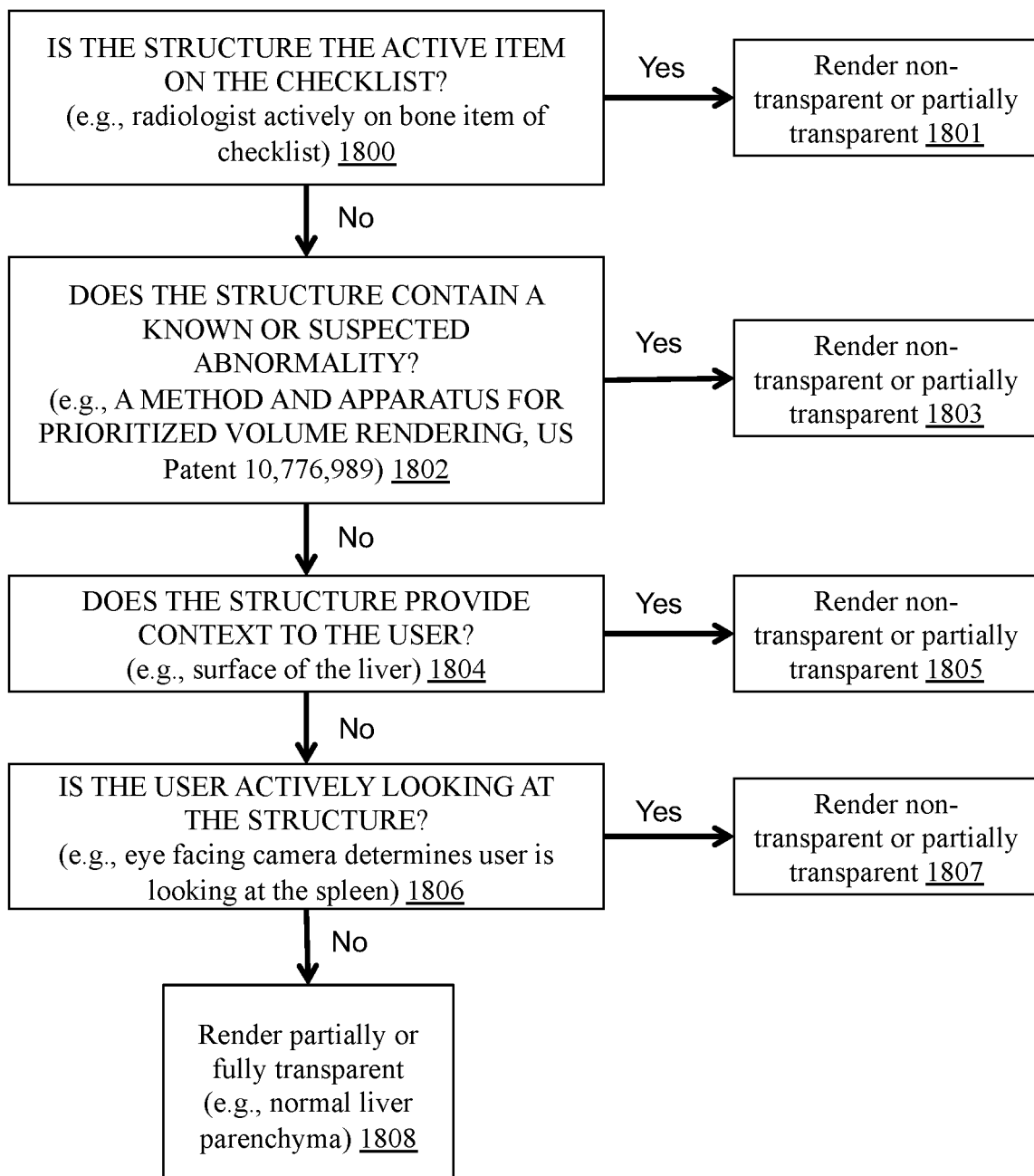
FIG. 18 illustrates a method of determining which structures should be rendered non-transparent, partially transparent or fully transparent.

FIG. 18 illustrates a method of determining which structures should be rendered non-transparent, partially transparent or fully transparent. 1800 illustrates a processing block for determining whether or not the structure is the active item on the checklist. For example, the radiologist's checklist comprises many items (e.g., a CT scan of the abdomen contains the liver, spleen, gallbladder, etc.). 1801 illustrates a processing block which renders the structure non-transparent or partially transparent, which is performed if the structure is the active item on the checklist. 1802 illustrates a processing block for determining whether or not the structure contains a known or suspected abnormality. For example, this is discussed further in U.S. Pat. No. 10,776,989, A METHOD AND APPARATUS FOR PRIORITIZED VOLUME RENDERING. 1803 illustrates a processing block which renders the structure non-transparent or partially transparent, which is performed if the structure contains a known or suspected abnormality. 1804 illustrates a processing block for determining whether or not the structure provides context to the user. For example, the surface of the liver provides context to the user.

1805 illustrates a processing block which renders the structure non-transparent or partially transparent, which is performed if the structure provides context to the user. 1806 illustrates a processing block for determining whether the user is actively looking at a structure. For example, an eye facing camera can determine whether the user is looking at the spleen. 1807 illustrates a processing block which renders the structure non-transparent or partially transparent, which is performed if the structure is actively looking at the spleen. 1808 illustrates a processing block which renders partially or fully transparent (e.g., normal liver parenchyma).

Figure 19A:
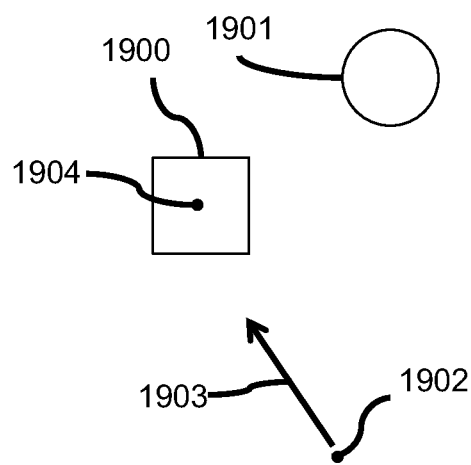
FIG. 19A is a top down view at a first time point showing a first viewing point, a first viewing angle and a first convergence point.

FIG. 19A is a top down view at a first time point showing a first viewing point, a first viewing angle and a first convergence point. 1900 illustrates a first segmented object. 1901 illustrates a second segmented object. 1902 illustrates a first viewing location. 1903 illustrates a first viewing angle. 1904 illustrates a first convergence point.

Figure 19B:
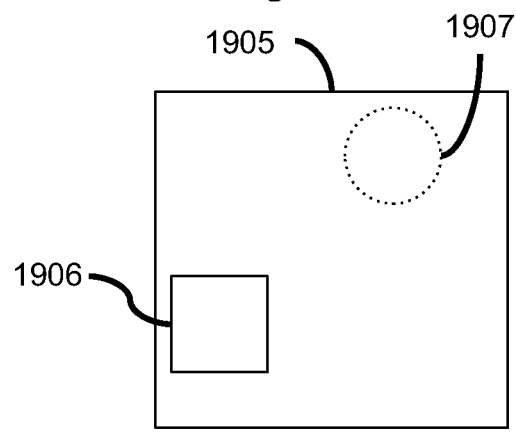
FIG. 19B illustrates a rendered image from FIG. 19A displayed at the first time point.

FIG. 19B illustrates a rendered image from FIG. 19A displayed at the first time point. 1905 illustrates a rendered image from FIG. 19A. A prioritization scheme is utilized. Since the convergence point 1904 is focused on object 1900, as shown in FIG. 19A, object 1900 will be displayed with its optimized rendering scheme, which in this example is voxel rendering. 1906 illustrates an image of the first segmented object 1900 from FIG. 19A, which utilizes an optimized volume rendering strategy and is displayed in the most optimized fashion possible. Assume that the optimized volume rendering strategy for object 1900 from FIG. 19A is voxel rendering.

Assuming this, then object 1900 in FIG. 19A will be rendered using a voxel rendering strategy. This data can be stored for later use, see FIG. 19E below. At this juncture, the other portions of the volume may or may not be rendered with their most optimum type of rendering. If the processor is fast enough to display all objects with their most optimum type of rendering, then each object (e.g., segmented structure) will be rendered with its most optimum type of rendering. If not, then some objects in the volume will be given a lower tiered rendering strategy. In this time point, object 1901 is given a lower tiered rendering strategy. The #1 preferred rendering type for object 1901 is voxel rendering; however, since the processor is not fast enough to display object 1901 with the #1 preferred rendering type (e.g., voxel rendering), object 1901 is therefore rendered as a lower preference type of rendering (e.g., point cloud). 1907 illustrates the second segmented object from FIG. 19A, which utilizes an non-optimized volume rendering strategy.

Figure 19C:
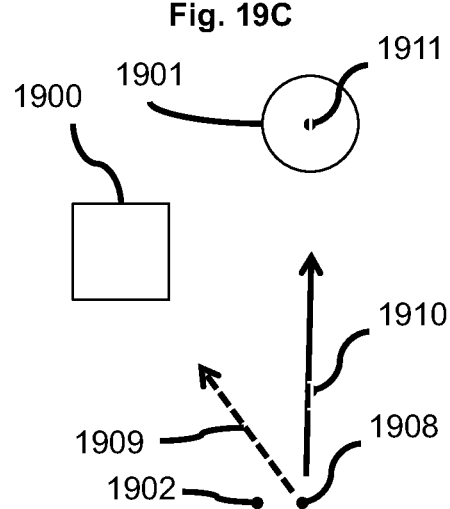
FIG. 19C is a top down view at a second time point showing a second viewing point and a simulated viewing angle towards the first segmented object, and a second viewing angle towards the second segmented object.

FIG. 19C is a top down view at a second time point showing a second viewing point and a simulated viewing angle towards the first segmented object, and a second viewing angle towards the second segmented object. 1900 illustrates the first segmented object. 1901 illustrates the second segmented object. 1902 illustrates the first viewing location. 1908 illustrates the second viewing location (which has moved in location (e.g., x,y,z coordinate) as compared to the first viewing location in FIG. 19A). 1909 illustrates a first simulated viewing angle from the second viewing location 1908 to the first segmented object 1910. The term "simulated viewing angle" is used because the user is not actually looking at this location at this moment in time. Rather the user is looking at the second segmented object 1901. The purpose of generating the first simulated viewing angle is to help generate at least a portion of the image of the first segmented object 1900. 1910 illustrates the second viewing angle from the second viewing location 1908 to the second segmented object 1901. 1911 illustrates the second convergence point. In this example, the viewing location changes (e.g., in a HDU with head tracking, some head movement occurs).

Figure 19D:
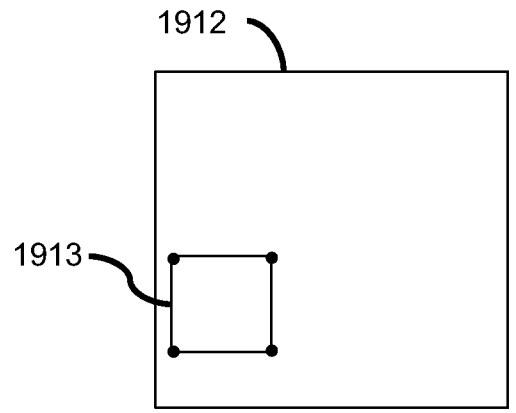
FIG. 19D illustrates a modified image of the first segmented object based on the first simulated viewing angle.

FIG. 19D illustrates a modified image of the first segmented object based on the first simulated viewing angle. 1912 illustrates an image display. 1913 illustrates an image of the first segmented object 1901. Note that this image 1912 can be generated by modifying the image 1906 of the first segmented object 1900 from FIG. 19A. Examples of modifications include warping or coloring the image. Therefore this portion of the image is generated by using a portion of the previous rendered image 1905, not by performing rendering. This portion of the image 1912 is stored and used later. This is useful because it provides a reasonably good image, but does not require the high image processing requirements of volume rendering.

Figure 19E:
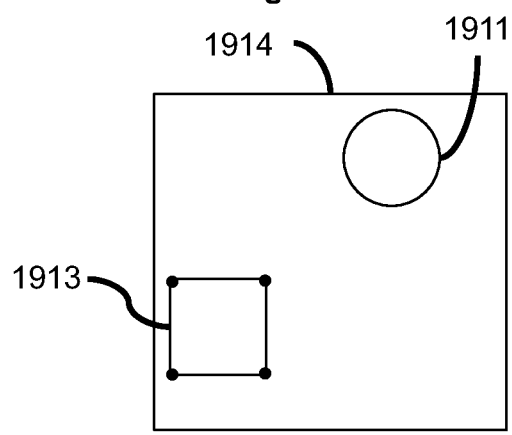
FIG. 19E illustrates a rendered image from FIG. 19C displayed at a second time point.

FIG. 19E illustrates a rendered image from FIG. 19C displayed at a second time point. 1914 illustrates a rendered image from FIG. 19C. A prioritization scheme is utilized. Since the second convergence point 1911 is focused on the second segmented object 1901, as shown in FIG. 19C, object 1901 will be displayed with its optimized rendering scheme, which in this example is voxel rendering.

1915 illustrates an image of the second segmented object 1901 from FIG. 19C, which utilizes an optimized volume rendering strategy and is displayed in the most optimized fashion possible. Assume that the optimized volume rendering strategy for object 1901 from FIG. 19C is voxel rendering. Assuming this, then object 1901 in FIG. 19C will be rendered using a voxel rendering strategy.

At this juncture, the other portions of the volume may or may not be rendered with their most optimum type of rendering. If the processor is fast enough to display all objects with their most optimum type of rendering, then each object (e.g., segmented structure) will be rendered with its most optimum type of rendering. If not, then some objects in the volume will be given a lower tiered rendering strategy.

In this time point, object 1900 is given a lower tiered rendering strategy. In this example, the strategy implemented is to use the image 1913 of the first segmented object 1901 generated in FIG. 19D. This is useful because it provides a reasonably good image, but does not require the high image processing requirements of volume rendering.

Figures 20A, 20B:
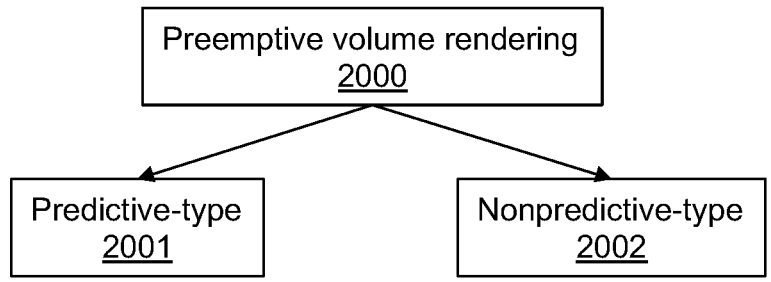
FIG. 20A illustrates preemptive volume rendering.
FIG. 20B illustrates an example set of 5 images based on theoretical viewing parameters.

FIG. 20A illustrates preemptive volume rendering. 2000 illustrates a text box, which illustrates preemptive volume rendering. The preemptive type volume rendering is a rendering process which generates a rendered image from a set of viewing parameters prior to the viewing parameters being met by the user. There are two types of preemptive volume rendering. 2001 illustrates the predictive-type preemptive volume rendering. For example, a future location of a digital marker can be utilized in conjunction with the predictive-type preemptive volume rendering (e.g., see FIG. 18A-D on U.S. Pat. No. 10,712,837, which is incorporated by reference in its entirety). Alternatively, the user's head movements or eye movements could be predicted through techniques, such as using artificial intelligence algorithms. 2002 illustrates the nonpredictive-type volume rendering. Nonpredictive-type volume rendering would include generating a large volume of points. The overall preemptive volume rendering strategy could utilize off site volume rendering (e.g., in the cloud) and then perform high speed downloads (e.g., 5G) to the user.

FIG. 20B illustrates an example set of 5 images based on theoretical viewing parameters. Example viewing parameters include, but are not limited to the following: viewpoint(s) (note: can perform a single viewpoint for viewing on a 2D monitor or two viewpoints for viewing on a head display unit per U.S. Pat. No. 8,384,771); viewing angle(s) towards convergence point; horizontal field of view; vertical field of view; visualization settings of the volume of interest (e.g., filtering, type of rendering, grayscale settings such as window/level, color settings, any voxel manipulations, etc.). A text box is illustrated showing 5 images, which are stored in a look up table. For example, the first row illustrates image "1", which can be displayed when the viewing parameters of viewpoint (x=100, y=100, z=100), viewing angle ($\alpha$=90°, $\Theta$=0°) and the volume of the vasculature of the brain only are met. For example, the second row illustrates image "2", which can be displayed when the viewing parameters of viewpoint (x=101, y=100, z=100), viewing angle ($\alpha$=90°, $\Theta$=0°) and the volume of the vasculature of the brain only are met. For example, the third row illustrates image "3", which can be displayed when the viewing parameters of viewpoint (x=102, y=100, z=100), viewing angle ($\alpha$=90°, $\Theta$=0°) and the volume of the vasculature of the brain only are met.

For example, the fourth row illustrates image "4", which can be displayed when the viewing parameters of viewpoint (x=100, y=100, z=100), viewing angle ($\alpha$=90°, $\Theta$=0°) and the volume of the vasculature of the brain only are met. For example, the fifth row illustrates image "5", which can be displayed when the viewing parameters of viewpoint (x=100, y=100, z=100), viewing angle ($\alpha$=90°, $\Theta$=0°) and the volume of the vasculature of the brain only are met.

Figure 21:
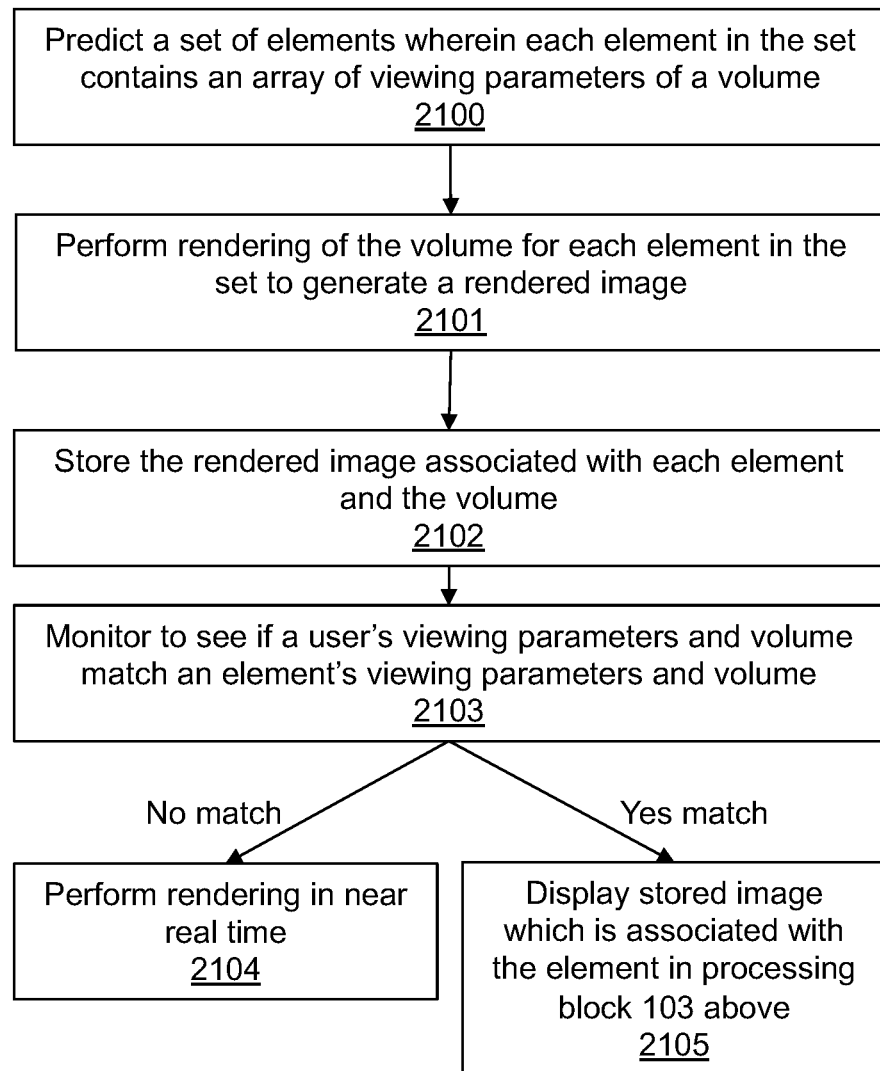
FIG. 21 illustrates predictive-type preemptive volume rendering.

FIG. 21 illustrates predictive-type preemptive volume rendering. 2100 illustrates a processing block of predicting a set of elements wherein each element in the set contains an array of viewing parameters of a volume. For example, a future location of a digital marker can be utilized in conjunction with the predictive-type preemptive volume rendering (e.g., see FIG. 18A-D on U.S. Pat. No. 10,712,837, which is incorporated by reference in its entirety). In essence, the goal of this step is to predict upcoming likely viewing parameters. A first strategy for predicting sets of viewing parameters is by head location. For example, a small tilt in a user's head position is a common movement during the viewing process. Therefore, a set of images can be rendered for a radius of viewpoints around the current viewpoint. A second strategy for predicting sets of viewing parameters is by eye movement patterns. For example, if a user typically views a structure from bottom to top, this typical viewing pattern can be utilized to predict which images to preemptively render. Other strategies include, but are not limited to using imaging features, checklists, and other. If a predictive strategy is not performed, this process would be referred to as nonpredictive preemptive volume rendering. 2101 illustrates a processing block of performing rendering of the volume for each element in the set to generate a rendered image. 2102 illustrates a processing block of storing the rendered image associated with each element and the volume. 2103 illustrates a processing block of monitoring to see if a user's viewing parameters and volume match an element's viewing parameters and volume. 2104 illustrates a processing block of performing rendering in near real time, which is performed if there is no match. 2105 illustrates a processing block of displaying the stored image which is associated with the element in processing block 2103 above, which is performed if there is a match. During the time when processing block 2105 is being performed, additional predictive-type preemptive volume rendering can be performed.

Figure 22:
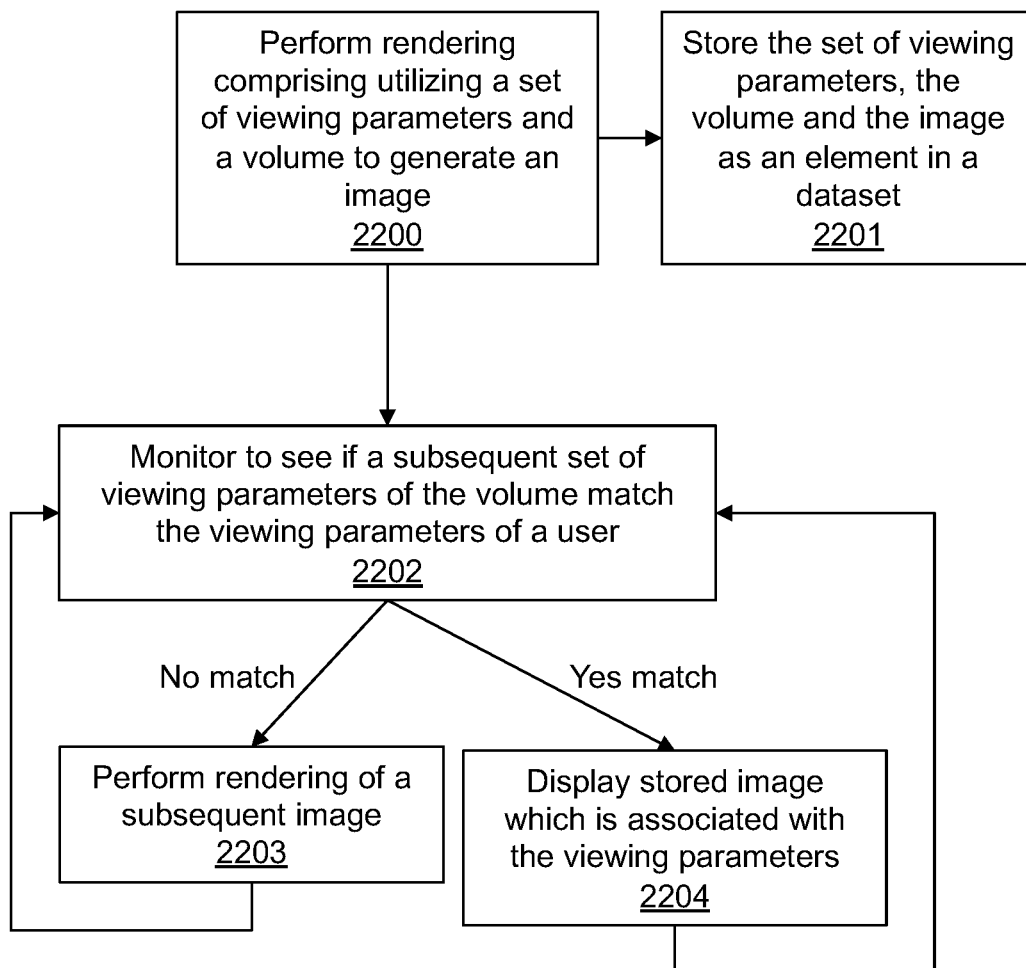
FIG. 22 illustrates a process for recall volume rendering.

FIG. 22 illustrates a process for recall volume rendering. 2200 illustrates the processing block of performing rendering comprising utilizing a set of viewing parameters and a volume to generate an image. 2201 illustrates the processing block of storing the set of viewing parameters, the volume and the image as an element in a dataset. 2202 illustrates the processing block of monitoring to see if a subsequent set of viewing parameters of the volume matches the viewing parameters stored in the dataset in processing block 2201. 2203 illustrates the processing block of performing rendering of a subsequent image, which is performed if the subsequent set of viewing parameters of the volume in processing block 2202 do not match a set of viewing parameters in the dataset in processing block 2201. 2204 illustrates the processing block of displaying a stored image, which is if the subsequent set of viewing parameters of the volume in processing block 2202 match a set of viewing parameters in the dataset stored in processing block 2201.

Figure 23:
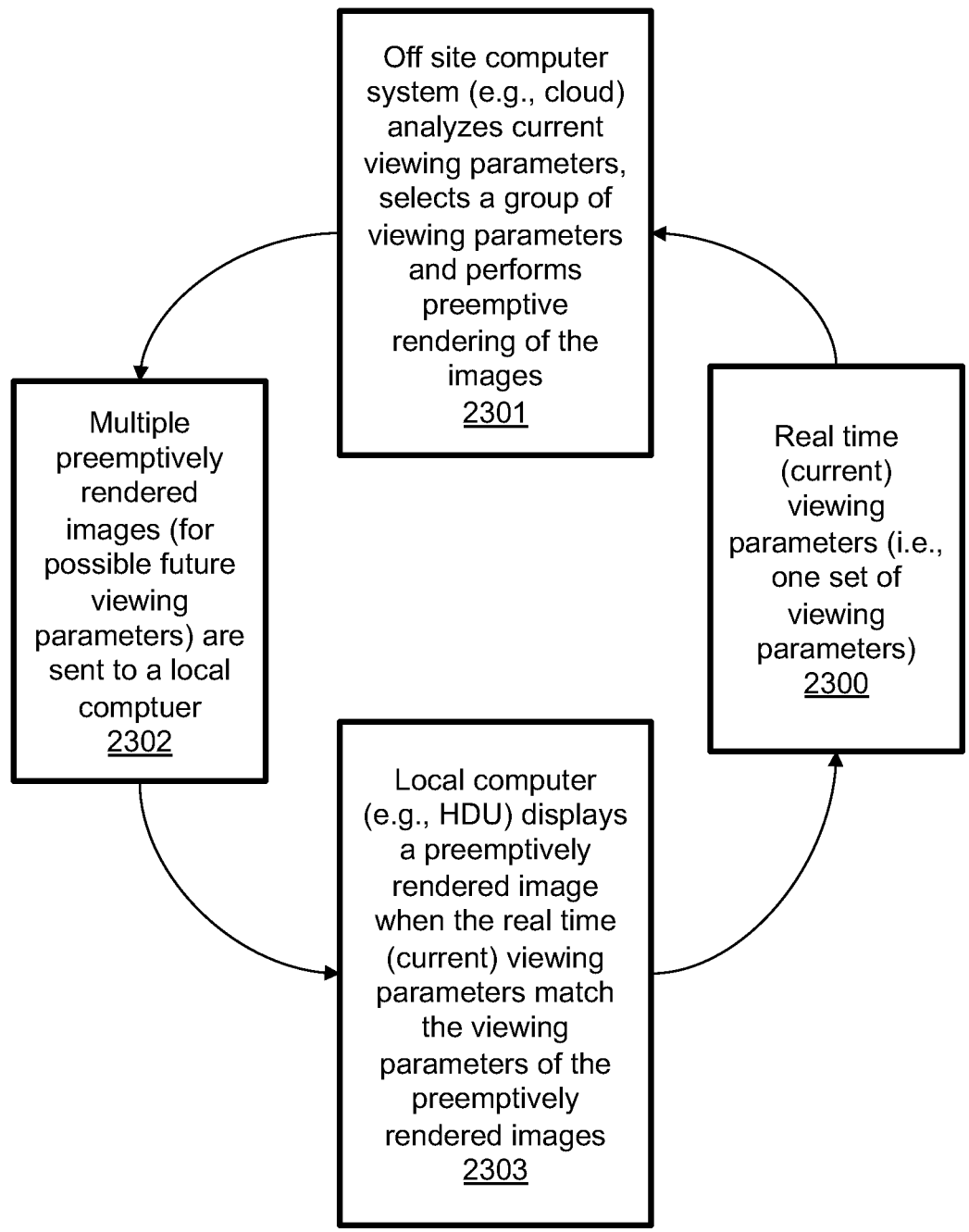
FIG. 23 illustrates a preemptive rendering technique, which utilizes an off site computer system.

FIG. 23 illustrates a preemptive rendering technique, which utilizes an off site computer system. 2300 illustrates a processing block of sending a real time (current) viewing parameters (i.e., one set of viewing parameters) from a local computer. Note that this local computer may be on board a head display unit (e.g., HoloLens) or used in conjunction with a head display unit (e.g., Oculus). 2301 illustrates a processing block of analyzing by off site computer system (e.g., cloud) the current viewing parameters, selecting a group of viewing parameters and performing preemptive rendering of the images. 2302 illustrates a processing block of sending the multiple preemptively rendered images (for possible future viewing parameters) to a local computer. 2303 illustrates a processing block of the local computer (e.g., HDU) displaying a preemptively rendered image when the real time (current) viewing parameters match the viewing parameters of the preemptively rendered images.

Throughout the entirety of the present disclosure, use of the articles "a" or "an" to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. The device(s) or computer systems that integrate with the processor(s) may include, for example, a personal computer(s), workstation(s) (e.g., Sun, HP), personal digital assistant(s) (PDA(s)), handheld device(s) such as cellular telephone(s), laptop(s), handheld computer(s), or another device(s) capable of being integrated with a processor(s) that may operate as provided herein. Accordingly, the devices provided herein are not exhaustive and are provided for illustration and not limitation. References to "a microprocessor and "a processor, or "the microprocessor and "the processor." may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor or "processor terminology may thus also be understood to include a central processing unit, an arithmetic logic unit, an application-specific integrated circuit (IC), and/or a task engine, with such examples provided for illustration and not limitation. Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where Such memory may be contiguous and/or partitioned based on the application. Accordingly, references to a database may be understood to include one or more memory associations, where such references may include commercially available database products (e.g., SQL, Informix, Oracle) and also include proprietary databases, and may also include other structures for associating memory Such as links, queues, graphs, trees, with such structures provided for illustration and not limitation. References to a network, unless provided otherwise, may include one or more intranets and/or the Internet, as well as a virtual network. References hereinto microprocessor instructions or microprocessor-executable instructions, in accordance with the above, may be understood to include programmable hardware.

Unless otherwise stated, use of the word "substantially' may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art. Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method of rendering and displaying a volumetric dataset comprising:
dividing said volumetric dataset into a first portion and a second portion wherein said first portion is stored in a data file and said second portion is stored in said data file;
performing a first type of rendering for the first portion wherein said first type of rendering comprises one of a group consisting of:
rendering said first portion of said volumetric dataset as voxels;
rendering said first portion of said volumetric dataset as a point cloud; and
rendering said first portion of said volumetric dataset as polygon mesh;
performing a second type of rendering for the second portion wherein said first type of rendering is different from said second type of rendering and wherein said second type of rendering comprises one of a group consisting of:
rendering said second portion of said volumetric dataset as voxels;
rendering said second portion of said volumetric dataset as a point cloud; and
rendering said second portion of said volumetric dataset as polygon mesh; and
displaying an image to a user wherein said first portion of said image is rendered with said first type of rendering and said second portion of said image is rendered with said second type of rendering.

2. The method of claim 1 further comprising wherein the first type of rendering has a first processing speed and the second type of rendering has a second processing speed.

3. The method of claim 1 further comprising wherein the first portion is determined by a radius around a user's convergence point.

4. The method of claim 1 further comprising wherein the first portion is determined by a segmented object located at user's convergence point.

5. The method of claim 1 further comprising wherein the first portion is determined a binocular field of view and wherein the second portion is determined by a monocular field of view.

6. The method of claim 1 further comprising wherein the first portion is determined by a segmented item on a checklist.

7. The method of claim 1 further comprising wherein the first portion is determined by a location within the volume.

8. The method of claim 1 further comprising wherein the first portion is determined by an artificial intelligence algorithm.

9. The method of claim 1 further comprising wherein the first portion is determined by a prioritization level of an object.

10. The method of claim 1 further comprising wherein the first portion is determined by at least one of the group consisting of: an imaging feature of a segmented object; and, a combination of imaging features of a segmented object.

11. The method of claim 1 further comprising wherein the first type of rendering is optimized for the first portion and the second type of rendering is optimized for the second portion.

12. The method of claim 1 further comprising wherein the first portion is determined in a dynamic fashion.

13. The method of claim 1 further comprising wherein the first portion is determined by a location within a field of view.

14. The method of claim 1 further comprising wherein the first portion is rendered in at least one of the group consisting of: partial transparent rendering; and, fully transparent rendering.

15. The method of claim 1 further comprising performing predictive type preemptive volume rendering comprising the steps of:
generating a predicted set of viewing parameters;
rendering the volumetric dataset using the predicted set of viewing parameters to create an image; and
displaying the image when the user's viewing parameters match the predicted set of viewing parameters.

16. The method of claim 1 further comprising performing recall type volume rendering comprising the steps of:
storing a rendered image and a set of viewing parameters associated with the rendered image;
monitoring the user's viewing parameters; and
displaying the rendered image when the user's viewing parameters match the set of viewing parameters associated with the rendered image.

17. The method of claim 1 further comprising displaying said image on a display.

18. The method of claim 17 further comprising wherein the display is a head display unit.

19. A non-transitory computer readable medium having computer readable code thereon for image processing, the medium comprising:
instructions for dividing a volumetric dataset into a first portion and at least one additional portion wherein said first portion is stored in a data file and said at least one additional portion is stored in said data file;
instructions for performing a first type of rendering for the first portion wherein said first type of rendering comprises one of a group consisting of:
rendering said first portion of said volumetric dataset as voxels;
rendering said first portion of said volumetric dataset as a point cloud; and
rendering said first portion of said volumetric dataset as polygon mesh;
instructions for performing at least one additional type of rendering for the at least one additional portion wherein said first type of rendering is different from said at least one additional type of rendering and wherein said at least one additional type of rendering comprises at least one of a group consisting of:
rendering said at least one additional portion of said volumetric dataset as voxels;
rendering said at least one additional portion of said volumetric dataset as a point cloud; and
rendering said at least one additional portion of said volumetric dataset as polygon mesh; and
instructions for displaying an image to a user wherein said first portion of said image is rendered with said first type of rendering and said at least one additional portion of said image is rendered with said at least one additional type of rendering.

20. An apparatus comprising:
a processor;
a non-transitory memory having computer-executable instructions stored thereupon which, when executed by the processor, cause the processor to perform:
dividing a volumetric dataset into a first portion and at least one additional portion wherein said first portion is stored in a data file and said at least one additional portion is stored in said data file;
performing a first type of rendering for the first portion wherein said first type of rendering comprises one of a group consisting of:
rendering said first portion of said volumetric dataset as voxels;
rendering said first portion of said volumetric dataset as a point cloud; and
rendering said first portion of said volumetric dataset as polygon mesh; and
performing at least one additional type of rendering for the at least one additional portion wherein said first type of rendering is different from said at least one additional type of rendering and wherein said at least one additional type of rendering comprises at least one of a group consisting of:
rendering said at least one portion of said volumetric dataset as voxels;
rendering said at least one portion of said volumetric dataset as a point cloud; and
rendering said at least one portion of said volumetric dataset as polygon mesh; and
displaying an image to a user wherein said first portion of said image is rendered with said first type of rendering and said at least one additional portion of said image is rendered with said at least one additional type of rendering.

\* \* \* \* \*